United States Patent [19]

Douglass

[11] Patent Number: 5,798,258
[45] Date of Patent: Aug. 25, 1998

[54] CART PROTEIN AND DNA ENCODING THEREFOR

[75] Inventor: James O. Douglass, Thousand Oaks, Calif.

[73] Assignee: Oregon Health Sciences University, Portland, Oreg.

[21] Appl. No.: 434,705

[22] Filed: May 4, 1995

[51] Int. Cl.$^6$ .............................. C12N 1/20; C12N 15/00; C07H 17/00; C07K 14/00
[52] U.S. Cl. .................. 435/252.3; 435/69.1; 435/320.1; 435/325; 536/23.1; 530/350
[58] Field of Search ........................ 536/23.1; 435/320.1, 435/240.1, 69.1, 325, 252.3; 530/350

[56] References Cited

PUBLICATIONS

Gawin, "Cocaine Addition: Psychology and Neurophysiology," *Science* 251:1580–1586 (1991).
Spiess et al., "Isolation and Sequence Analysis of a Somatostatin–like Polypeptide from Ovine Hypothalamus," *Biochemistry* 20:1982–1988 (1981).
Kuhar et al., "The Dopamine Hypothesis of the Reinforcing Properties of Cocaine," *Trends in Neuroscience* 14:299–302 (1991).
Nestler, "Molecular Mechanisms of Drug Addiction," *J. Neuroscience* 12:2439–2450 (1992).
Graybiel et al., "Amphetamine and Cocaine Induce Drug–Specific Activation of the c–fos Gene in Striosome––Matrix Compartments and Limbic Subdivisions of the Striatum," *Proc. Natl. Acad. Sci. USA* 87:6912–6916 (1990).
Dragunow et al., "3.4 MethyleneDioxyMethamphetamine Induces Fos–like Proteins in Rat Basal Ganglia: Reversal With MK–801," *Eur. J. Pharmacol.* 206:255–258 (1991).
Hope et al., "Regulation of Immediate Early Gene Expression and AP–1 Binding in the Rat Nucleus Accumbens by Chronic Cocaine," *Proc. Natl. Acad. Sci. USA* 89:5764–5768 (1992).
Nguyen et al., "Differential Expression of c–Fos and Zif268 in Rat Striatum After Haloperidol, Clozapine and Amphetamine," *Proc. Natl. Acad. Sci. USA* 89:4270–4274 (1992).
Young et al., "Cocaine Induces Striatal c–Fos–Immunoreactive Proteins via Dopaminergic $D_1$ Receptors," *Proc. Natl. Acad. Sci. USA* 88:1291–1295 (1991).
Iadarola et al., "Induction and Suppression of Proto–Oncogenes in Rat Striatum After Single and Multiple Treatments with Cocaine and GBR–12909." In *NIDA research monograph series: Activation of immediate early genes by drugs of abuse* (Grzanna et al., Eds.), 125:181–211 (1993).

Clark et al., "Expression of c–fos mRNA in Acute and Kindled Cocaine Seizures in Rats," *Brain Res.* 582:101–106 (1992).
Couceyro et al., "Cocaine Differentially Regulates Activator Protein–1 mRNA Levels and DNA–Binding Complexes in the Rat Striatum and Cerebellum," *Mol. Pharmacol.* 46:667–676 (1994).
Liang and Pardee, "Differential Display of Eukaryotic Messenger RNA by Means of the Polymerase Chain Reaction," *Science* 257:967–971 (1992).
Liang et al., "Distribution and Cloning of Eukaryotic mRNAs by Means of Differential Display: Refinements and Optimization," *Nucleic Acids Res.* 21:3269–3275 (1993).
Bauer et al., "Identification of Differentially Expressed mRNA Species by an Improved Display Technique (DDRT–PCR)," *Nucleic Acids Res.* 21:4272–4280 (1993).
Van Slyke et al., "[4] Use of Vaccinia Virus to Study Neuropeptide Processing," *Methods in Neuroscience*, vol. 23: *Peptidases and Neuropeptide Processing* (A.I. Smith, Ed.), Academic Press, Inc., San Diego, CA, pp. 65–93 (1995.
Douglass et al., "PCR Differential Display Identifies a Rat Brain mRNA that is Transcriptionally Regulated by Cocaine and Amphetamine," *J. Neurosci.* 15:2471–2481 (1995).
Douglass et al 1996 Gene 169:241–245.
Sanbrook et al 1989 Molecular Cloning, A Laboratory Manual. Cold Spring Harbor Laboratory Press, Cold Spring Harbor, Ny p. 2.53

*Primary Examiner*—Karen Carlson
*Attorney, Agent, or Firm*—Christensen O'Connor Johnson & Kindness PLLC

[57] ABSTRACT

Disclosed are DNA sequences encoding to cocaine and amphetamine regulated (CART) proteins, polypeptide products of recombinant expression of these DNA sequences, peptides whose sequences are based upon the amino acid sequences deduced from these DNA sequences, antibodies specific for such proteins and peptides, procedures for the detection and quantitation of such proteins and nucleic acids related thereto, as well as procedures relating to the development of bacteriolytic methods, therapeutic agents, and compositions utilizing CART proteins.

10 Claims, 8 Drawing Sheets

```
AGCGAGGAAGTCCAGCACCATGGAGAGCTCCCGCCTGCGCTGCTACCCGTCCTGGGCGC          60
                  M   E   S   S   R   L   R   C   Y   P   V   L   G   A    14

CGCCCTACTGCTGCTGCTACCTTTGCTGGGTGCCGGTGCCGGAGCAGGAGGATGCCGAGCTGCA   120
 A   L   L   L   L   L   P   L   L   G   A   G   A   Q   E   D   A   E   L   Q    34
                    →                             ACGTCTCATG

GCCCCGAGCCCTGGACATCTACTCTGCCGTGGATGATGCGTCCCATGAFAAGGAGCTGCC       180
 P   R   A   L   D   I   Y   S   A   V   D   D   A   S   H   E   K   E   L   P    54

AAGGCGGCAACTTCGGGCTCCCCGGCTGTGTTGCAGATTGAAGCGCTGCAGGAAGTCCT        240
 R   R   Q   L   R   A   P   G   A   V   L   Q   I   E   A   L   Q   E   V   L    74

GAAGAAGCTCAAGAGTAAACGGCCATTCCGATCTATGAGAAGAAGTACGGCCAAGTCCCCAT    300
 K   K   L   K   S   K   R   I   P   I   Y   E   K   K   Y   G   Q   V   P   M    94

GTGTGACGCTGGAGAGCAGTGCGCAGTGCGCAGGATCGGGAAAGGGCCAGGATCGGGAAGCTGTGA  360
 C   D   A   G   E   Q   C   A   V   R   K   G   A   R   I   G   K   L   C   D    114
```

Fig. 1A.

```
CTGTCCCCGAGGAACTTCTTGCAATTCTTTCCTCTTGAAGTGCTTGTGAAGGGGTGACAG    420
 C  P  R  G  T  S  C  N  S  F  L  L  K  C  L  *                 129

CCTCCTTCGGTTCCCATATTTCCCTCTTTCCCCTAAAGGAGCGCTCTTTTGTCCCTGGAGC   480

CGCTTTAACAACAATAAAGTTTGCGTTCCCCCCAGAGAGTGGATGGGCTCTTTCCCTGCT    540
                                           ⇨
GCTTCAAAATAAAAAGATTTGATGTTATTGTGTGAAGGACAATACCTTGAATGGTGTTGGT   600
CGTTTTTTTTTT

ATGTGTGCAAAGTATTCTTCTCTCGTTTATCCACCTGACACATTCTTGTGACCTTTCTG    660

GGAAGAGAGGGACTTTCGCTTAAAACTGTATTTTTGTATGTGGCGGGTCACAATGAAG     720

ATTAGACCTAGTTAATTTTGGCAGATGACATCATAACCCGGAAAACAAATCACCCCAAAG   780
                                                      ⇨
CAACACAAATGGAAGCATGTGCAAATTACACCCCAATAAAGCATTTTGATAATTGCTCAC   840
```

Fig. 1B.

```
AACGACGAGTTTCAGAACGATGGAGAGCTCCCGCGTGAGGCTGCTGCCCCTCCTGGGCGC      60
                   M  E  S  S  R  V  R  L  L  P  L  L  G  A       14

CGCCCTGCTGCTGATGCTACCTCTGTTGGGTACCCGTGCCCAGGAGGACGCCGAGCTCCA    120
 A  L  L  L  M  L  P  L  L  G  T  R  A  Q  E  D  A  E  L  Q      34

GCCCCGAGCCCTGGACATCTACTCTGCCGTGGATGATGCCTCCCACGAGAAGGAGCTGAT    180
 P  R  A  L  D  I  Y  S  A  V  D  D  A  S  H  E  K  E  L  I      54

CGAAGGCGCTGCAAGAAGTCTTGAAGAAGCTCAAGAGTAAACGTGTTCCCATCTATGAGAA    240
 E  A  L  Q  E  V  L  K  K  L  K  S  K  R  V  P  I  Y  E  K      74

GAAGTATGGCCAAGTCCCCATGTGTGACGCCGGTGAGCAGTGTGCAGTGAGGAAGGGGC     300
 K  Y  G  Q  V  P  M  C  D  A  G  E  Q  C  A  V  R  K  G  A      94

AAGGATCGGGAAGCTGTGTGACTGTCCCCGAGGAACCTCCTGCAATTCCTTCCTCCTGAA    360
 R  I  G  K  L  C  D  C  P  R  G  T  S  C  N  S  F  L  L  K     114

GTGCTTATGAAGGGGCGTCCATTCTCCTCCATACATCCCTCTACTTTCCCCAGA          420
 C  L  *                                                         116
```

Fig. 2A.

```
GGACCACACCTTCCTCCCTGGAGTTTGGCTTAAGCAACAGATAAAGTTTTTATTTTCCTC   480

TGAAGGGAAAGGGCTCTTTTCCTGCTGTTTCAAAAATAAAGAACACATTAGATGTTACT    540

GTGTGAAGAATAAATGCCTTGTATGGTGTGTTGATACGTGTGTGTGAAGTATTCTTATTTTATTT  600

GTCTGACAAACTCTTGTACCTTTGTGTAAAGAAGGGAAGCTTTGTTTGAAAATTGTAT    660

TTTTGTATGTGGCATGGCAGAATGAAAATTAGATCTAGCTAATCTCGGTAGATGTCATTA  720

CAACCTGAAAATAAATCACCCTAAGTGACACAAATTGAAGCATGTACAAATTATACATA   780

ATAAAGTGTTTTTAATAATT (poly-A tail)                            800
```

*Fig. 2B.*

```
                                                    cccggggccctcctccaccccccttcctcttcgctcctccctcttcctgcacgggggg +1
ctcgggctcactataaaaggtgtgggagcgcgtggtgccccagcAACGACGAGTTTCAGAAC GATGGAGAGCTCCCGCGTGAGGCTGCTGCCCCTCCTGGGCGCCCTGCTGCTGATGCT
1     M  E  S  S  R  V  R  L  L  P  L  L  G  A  A  L  L  L  M  L ACCTCTGTTGGGTACCCGTGCCCAGGAGGACGCCGAGCTCCAGCCCCGAGCCCTGGACAT
21    P  L  L  G  T  R  A  Q  E  D  A  E  L  Q  P  R  A  L  D  I CTACTCTGCCGTGGATGATGCCTCCCACGAGAAGGAGCTGgtcggtattcccctcgctct
41    Y  S  A  V  D  D  A  S  H  E  K  E  L cgaccccccttgacgtgtcgccttgtctct ---- intron  (~425 bp) ----- gctgggctcgcagcaaggcgcaacttcaggctccgaagcggtgtgttgcagATCGAAGCG
54                                                      I  E  A
```

Fig. 3A.

```
 57  CTGCAAGAAGTCTTGAAGAAGAAGCTCAAGAGTAAACGTGTTCCCATCTATGAGAAGAAGTAT
      L   Q   E   V   L   K   K   K   L   K   S   K   R   V   P   I   Y   E   K   K   Y

77  GGCCAAGTCCCCATGgtaaggtttgtggtcactccctccgtgttttccaagagaaag
      G   Q   V   P   M 82  tacac ---- intron (~540 bp) ---- gggaacctgggtttgttcatactcg
     atgaccacacatttgtttcagTGTGACGCCGGTGAGCAGTGTGCAGTGAGGAAAGG
                          C   D   A   G   E   Q   C   A   V   R   K   G 94  GGCAAGGATCGGGAAGCTGTGTGACTGTCCCCGAGGAACCTCCTGCAATTCCTTCCTCCT
      A   R   I   G   K   L   C   D   C   P   R   G   T   S   C   N   S   F   L   L 114  GAAGTGCTTATGAAGGGGGCGTCCAATTCTCCTCCATACATCCCCATCCCCTACTTTCCCC
      J   C   K   *
```

Fig. 3B.

```
AGAGGACCACACCTTCCTCCCTGGAGTTTGGCTTAAGCAACAGATAAAGTTTTATTTTC
CTCTGAAGGGAAAGGGCTCTTTTCCTGCTGTTTCAAAAATAAAAGAACACATTAGATGTT
ACTGTGTGAAGAATAAATGCCTTGTATGGTGTTGATACGTGTGTGAAGTATTCTTATTTA
TTTGTCTGACAAACTCTTGTGTACCTTTGTGTAAAGAAGGGAAGCTTTGTTTGAAAATTG
TATTTTGTATGTGGCATGGCAGAATGAAAATTAGATCTAGCTAATCTCCGTAGATGTCA
TTACAACCTGGAAAATAAATCACCCTAAGTGACACAAATTGAAGCATGTACAAATTATAC
ATAATAAAGTGTTTTAATAATT(An)gcccatagtgcactgctgtttcatataagtaa
tttaagtggaaatggtgagattaatcatgctgttgttttcaaagaaaatatttcaaaaa
tagcagcctattggaaatgcactacgtcagagttgatcg
```

CART PROTEIN AND DNA ENCODING THEREFOR

This invention was funded in part by the National Institutes of Health through the National Institute on Drug Abuse under Grant No. RO1 DA04154. The government has certain rights in the invention.

FIELD OF THE INVENTION

The present invention relates generally to Cocaine and Amphetamine Regulated Transcript (CART) proteins and more particularly to mammalian CART proteins, to DNA sequences encoding CART proteins, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and nucleic acids related thereto, as well as to procedures relating to the development of therapeutic agents utilizing CART proteins.

BACKGROUND OF THE INVENTION

Cocaine is a psychomotor stimulant affecting mammalian physiology and behavior following both acute and chronic patterns of administration. These adaptive changes result in the establishment of physical states representing tolerance, dependence, sensitization and withdrawal. Pharmacologically, the drug acts by inhibiting the synaptosomal uptake of catecholamines (including dopamine and norepinephrine), and serotonin (Gawin, "Cocaine Addiction: Psychology and Neurophysiology," *Science*, 251:1580–1586 (1991); Koob, "Drugs of Abuse: Anatomy, Pharmacology and Function of Reward Pathways," *Trends in Neuroscience*, 13:177–184 (1992)). Modulation of dopaminergic neurotransmission within the striatum, for example, is believed to underlie the rewarding and reinforcing properties associated with cocaine administration (Kuhar et al, "The Dopamine Hypothesis of the Reinforcing Properties of Cocaine" *Trends in Neuroscience*, 14:299–302 (1991)).

It is currently hypothesized that cellular plasticity within specific neural circuits underlies the behavioral and physiological alterations associated with psychomotor stimulant administration (for review, see Nestler, "Molecular mechanisms of drug addiction," *J Neuroscience* 12:2439–2450 (1992)). One such type of plasticity occurs at the nuclear level, and involves the regulated expression of specific sets of genes. For example, cocaine selectively regulates the pattern of expression of immediate early genes (IEGs), particularly those belonging to the Fos and Jun (i.e., AP-1) family of transcriptional regulatory factors, within the brain. Furthermore, such transcriptional regulation appears to be localized to those brain regions regulated by catecholaminergic input. For example, it is now firmly established that acute administration of cocaine induces expression of c-fos and jun B mRNA in the rat striatum (Graybiel et al., "Amphetamine and Cocaine Induce Drug-Specific Activation of the c-fos Gene in Striosome-Matrix Compartments and Limbic Subdivisions of the Striatum," *Proc. Natl. Acad. Sci. USA*, 87:6912–6916 (1990); Dragunow et al., "3,4 MethyleneDioxyMethamphetamine Induces Fos-like Proteins in Rat Basal Ganglia: Reversal With MK-801," *Eur. J Pharmacol.*, 206:255–258 (1991); Hope et al., "Regulation of Immediate Early Gene Expression and AP-1 Binding in the Rat Nucleus Accumbens by Chronic Cocaine," *Proc. Natl. Acad. Sci. USA*, 89:5764–5768 (1992); Nguyen et al., "Differential Expression of c-Fos and Zif-268 in Rat Striatum After Haloperidol, Clozapine and Amphetamine," *Proc. Natl. Acad. Sci. USA*, 89:4270–4274 (1992); Young et al., "Cocaine Induces Striatal c-fos-Immunoreactive Proteins via Dopaminergic D1 Receptors," *Proc. Natl. Acad. Sci. USA*, 88:1291–1295 (1991)), a brain structure regulated by catecholaminergic input and representing a crucial component of the neuronal circuitry underlying reward. The cerebellum also represents a brain structure in which c-fos mRNA levels are selectively elevated following acute cocaine administration (Iadarola et al., "Induction and Suppression of Proto-Oncogenes in Rat Striatum After Single and Multiple Treatments with Cocaine and GBR-12909," In *NIDA research monograph series: Activation of immediate early genes by drugs of abuse* (Grzanna et al., Eds.), 125:181–211 (1993); Clark et al., "Expression of c-fos mRNA in Acute and Kindled Cocaine Seizures in Rats," *Brain Res.*, 582:101–106 (1992)). Studies have further shown that cerebellar c-fos mRNA levels rapidly increase following acute cocaine treatment (Iadarola et al., supra; Clark et al., supra), with chronic treatment resulting in a sensitization of the transcriptional response (Couceyro et al., "Cocaine Differentially Regulates Activator Protein-i 1 mRNA Levels and DNA Binding Complexes in the Rat Striatum and Cerebellum," *Mol. Pharmacol.*, 46:667–676 (1994)). Thus, transcriptional plasticity appears to represent a cellular mechanism through which specific neural networks respond and adapt to psychomotor stimulant administration. By contrast, the hippocampus represents a transcriptionally quiescent brain structure following acute administration of psychomotor stimulants. Thus, such brain region specific transcriptional changes associated with psychomotor stimulant administration are likely to be related to reinforcement and addiction.

An important area of current research involves identification of additional psychomotor stimulant regulated genes. Identification of such genes will increase our understanding of the molecular events underlying both short- and long-term cellular changes resulting from administration of psychomotor stimulant drugs, and may potentially lead to the development of therapeutic agents which mediate effects of psychomotor drugs.

SUMMARY OF THE INVENTION

In accordance with the present invention, differential display PCR techniques (Liang and Pardee, "Differential Display of Eukaryotic Messenger RNA by Means of the Polymerase Chain Reaction," *Science*, 257:967–971 (1992); Liang et al., "Distribution and Cloning of Eukaryotic mRNAs by Means of Differential Display: Refinements and Optimization," *Nucleic Acids Res.*, 21:3269–3275 (1993); Bauer et al., "Identification of Differentially Expressed mRNA Species by an Improved Display Technique (DDRT-PCR)," *Nucleic Acids Res.*, 21:4272–4280 (1993)) were used to obtain a cDNA representing a rat mRNA whose striatal levels are increased 4- to 5-fold following acute administration of cocaine or amphetamine. This mRNA (termed CART; Cocaine and Amphetamine Regulated Transcript) is either 700 or 900 bases in length depending on the site of poly(A) addition. A presumed alternate splicing event further generates diversity within the rat CART transcripts, and results in the presence or absence of an in-frame 39 base insert within the putative protein coding region. As a result, the predicted translation products are either 129 or 116 amino acids in length. Northern blot analysis of various rat tissues has determined that CART mRNA is expressed exclusively in neural and endocrine tissues, thus suggesting a functional role for the predicted protein within the neuroendocrine system. Features of the predicted protein include a prototypic signal sequence, suggesting that the protein is targeted for entry into the secretory pathway and thus serving as a neuroendocrine signaling molecule.

In addition to the rat CART cDNA and encoded CART protein, corresponding human hypothalamic cDNA and genomic clones were isolated. PCR/Southern blot analysis of DNA isolated from human/rodent somatic cell hybrid panels was employed to determine the chromosomal localization of the CART gene. Northern blot analysis was also used to determine the gross pattern of distribution of CART mRNA in human brain. The high degree of similarity at both the nucleic and amino acid level between rodent and human CART are suggestive of a conserved role within the mammalian neuroendocrine system.

Thus, the present invention relates generally to cocaine and amphetamine regulated transcript (CART) proteins and more particularly to mammalian CART proteins, to DNA sequences encoding CART proteins, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and nucleic acids related thereto, as well as to procedures relating to the development of therapeutic agents and pharmaceutical compositions utilizing CART proteins.

Association of DNA sequences provided by the invention with homologous or heterologous species expression control DNA sequences, such as promoters, operators, regulators, and the like, allows for in vitro transcription to form mRNA which, in turn, is susceptible to translation to provide CART proteins, and related poly- and oligopeptides in large quantities.

Also included within the invention is the incorporation of CART DNA sequences into procaryotic and eucaryotic host cells by standard transformation and transfection processes, involving suitable viral and circular DNA plasmid vectors, providing for useful proteins in quantities heretofore unavailable from natural sources.

In a presently preferred and illustrative DNA expression system of the invention, CART protein encoding DNA in pBluescript SK⁻ is PCR amplified and digested with BamHI and XhoI for ligation into the plasmid pZVneo. The plasmid DNA is then cloned into vaccinia virus (Van Slyke et al., "Use of Vaccinia Virus to Study Neuropeptide Processing," *Methods in Neuroscience*, Vol. 23: *Peptidases and Neuropeptide Processing*, A. I. Smith, Ed., Academic Press, San Diego, Calif. (1995)). The recombinant vaccinia virus, containing the CART protein encoding DNA, is used to infect mammalian cells, such as HeLa, BSC40 (African Green Monkey kidney) or AtT-20 (mouse anterior pituitary corticotroph) cells allowing for the production of a functional CART protein, demonstrating functional characteristics of native CART protein including for example, cross-reactivity with anti-serum to CART polypeptides.

In another representative DNA expression system of the invention, CART protein encoding DNA is ligated into bacterial plasmid pET15b or pET23b to obtain a pET/CART plasmid encoding a fusion protein comprising amino acids encoded by the original pET plasmid, as well as the entire CART sequence, minus the signal sequence. The pET/CART plasmid is then transformed in *Escherichia coli* allowing for transcription and translation to provide a functional CART protein having a molecular weight of about 14 kD and/or about 17 kD demonstrating functional characteristics of native CART proteins, including for example, cross-reactivity with anti-serum to CART polypeptides.

Novel protein products of the invention include polypeptides having the primary structural conformation (i.e., amino acid sequence) of rat or human CART protein, such as that set forth in FIGS. 1A–1B and 2A–2B as well as peptide fragments thereof, and synthetic peptides assembled to be duplicative of amino acid sequences thereof. Proteins, protein fragments, and synthetic peptides of the invention have numerous uses including therapeutic uses and provide the basis for preparation of monoclonal and polyclonal antibodies specifically immunoreactive with CART proteins. Antibodies of the invention can be used for affinity purification of CART proteins from other sources and cell types, as well as in the diagnostic quantification or qualification of CART proteins in human or animal biological samples.

The present invention also provides for procedures for the detection and/or quantification of normal, abnormal, or mutated forms, of CART proteins as well as nucleic acids (e.g., DNA and mRNA) associated therewith. In one illustrative embodiment, antibodies of the invention are employed in known immunological procedures for quantitative detection of CART proteins in samples, detection of DNA sequences of the invention (particularly those having sequences encoding CART proteins) that may be suitably labelled and employed for quantitative detection of mRNA encoding these proteins.

Among the multiple aspects of the present invention, therefore, is the provision of novel purified and isolated DNA sequences coding for expression of polypeptides having the characteristics of CART proteins (e.g., characterized by cross reactivity with antibodies to CART protein or peptides) and including: (a) novel CART proteins encoded by DNA sequences set out in FIGS. 1 and 2, as well as (b) DNA sequences which hybridize thereto under stringent hybridization conditions, i.e., of a stringency equal to or greater than the conditions described herein and employed in the initial isolation of DNAs of the invention, and (c) DNA sequences encoding the same, allelic variant, or analog CART protein or polypeptide fragments, through use of, at least in part, degenerate codons. Correspondingly provided are viral or circular plasmid DNA vectors incorporating such DNA sequences in procaryotic and eucaryotic host cells transformed or transfected with such DNA sequences and vectors, as well as novel methods for the recombinant production of CART proteins through cultured growth of such hosts and isolation of these proteins from the hosts or their culture media. Also, the CART protein DNA can be used as a probe in the detection and isolation of variants of CART proteins and analogs thereto. Diagnostic methods, therapeutic procedures, and pharmaceutical compositions which utilize CART proteins are also provided.

BRIEF DESCRIPTION OF THE DRAWINGS

The foregoing and other aspects and advantages of the invention will be apparent on consideration of the following detailed description and the accompanying drawings, wherein:

FIG. 1A and 1B are a representation of the nucleotide sequence of rat CART cDNA (SEQ ID No.:3). The corresponding rat CART amino acid sequence (SEQ ID No.:4) is also shown. The poly(A) addition site (AATAAA) utilized to generate the approximately 700 base rat CART transcript is underlined beginning at nucleotide 548. The poly(A) addition site utilized to generate the approximately 900 base rat CART transcript is underlined beginning at nucleotide 814. Open arrows represent the last nucleotide prior to the site of addition of the two respective poly(A) tails. FIG. 1A and 1B also show the location at which the 5' PCR differential display oligonucleotide hybridized (nucleotides 158 through 167) and the location at which the 3' PCR differential display oligonucleotide hybridized (nucleotides 544 through 556), as is described in Example 1. The translational reading frame begins with an ATG at nucleotide 20 and extends to the TGA termination site at nucleotide 407. The region representing an alternately spliced 39 nucleotide sequence is underlined at nucleotides 179 through 217. The presented nucleotide sequence has been assigned accession number U10071 by GenBank);

FIG. 2A and 2B are a representation of the nucleotide and amino acid sequence of human CART cDNA (SEQ ID No.:7), as described in Example 4. The poly(A) addition site (AATAAA) utilized to generate the approximately 900 base human CART transcript (nucleotides 780-785) is underlined. The translational reading frame begins with an ATG at nucleotide 20, and extends to the TGA termination site at nucleotide 368. The human CART cDNA sequence has been assigned accession number U16826 by GenBank, with the human CART genomic DNA sequence assigned accession number U20325;

FIG. 3A–3C are a representation of the nucleotide and amino acid sequence of human CART. For the nucleic acid sequence, capitalized letters represent nucleotides present in both cDNA and genomic DNA, while lower case letters represent nucleotides found only in genomic DNA. A putative promoter element (tataaa) is underlined at position −31. Only partial intron sequences are shown, with the complete intron size noted in ~bp, and the complete intron being set forth in SEQ ID No.:9. A 39 base sequence which is alternately spliced in rat CART mRNA is located at the 3' end of intron 1, and is italicized and underlined in FIG. 3A. The human CART mRNA cap site is located at nucleotide +1. Poly(A) addition sites (AATAAA) are underlined, with (A$_n$) representing location of the poly(A) tail. The predicted translational reading frame begins with an ATG at position +20 in the cDNA, and extends to the TGA termination site (*) at position 368. The human CART genomic DNA sequence has been assigned accession number U20325 by GenBank; and FIG. 4 is a direct comparison of the rat CART protein amino acid sequence (designated "r-", SEQ ID No.:4) with the human CART protein amino acid sequence (designated "h-", SEQ ID No.:8). Amino acid mismatches are shown by an asterisk (*). The underlined 13 amino acid sequence from amino acid 54 through amino acid 66 in the rat CART protein sequence is either present or absent due to an mRNA alternate splicing event.

DETAILED DESCRIPTION OF THE PREFERRED EMBODIMENT

In one aspect, the present invention provides a method of recovering CART protein in substantially pure form comprising the steps of removing the supernatant from unlysed cells that express CART protein, introducing the supernatant to an affinity matrix containing immobilized antibody capable of binding to CART protein, permitting the CART protein to bind to the antibody of the matrix, washing the matrix to remove unbound contaminants, and recovering the CART protein in substantially pure form by eluting said CART protein from said matrix.

The term "substantially pure" indicates a protein or composition that is essentially free of contaminants similar to the protein. In the present case, the normal contaminants associated with human CART protein predominately include human proteins. Thus, human CART protein is substantially pure if it is essentially free of human proteins. "Essentially free" is determined by weight. In general, a composition containing 70% or more by weight human CART protein and less than 30% of other human proteins may be considered substantially pure. Preferably, the composition will be at least 80% human CART protein, more preferably at least 90%, and most preferably at least 95% human CART protein. The presence of dissimilar components does not affect the determination of purity, thus a composition containing 0.7 mg/mL human CART protein in PBS will still be considered substantially pure if it contains less than 0.3 mg/mL other human proteins. In addition, further purification utilizing a lectin or wheat germ agglutinin column may be used before or after the antibody matrix step. Other purification steps could include, for example, sizing chromatography, ion chromatography, and gel electrophoresis. Further purification by velocity sedimentation through sucrose gradients may be used.

In another aspect of the invention, nucleotide sequences are provided that encode CART protein, as well as the use of such sequences or fragments thereof in the production of recombinant CART protein, as hybridization probes, or for other purposes.

In another aspect, the invention further includes a method for producing an antibody which is capable of binding to CART protein or DNA comprising the steps of preparing a peptide-protein or nucleotide-protein conjugate, said conjugate comprising at least 10, more preferably at least 14, and most preferably at least 18 consecutive amino acid or nucleic acid residues present in CART protein or DNA, immunizing an animal with said peptide-protein or nucleotide-protein conjugate, boosting the animals, and obtaining the antisera. In connection with this aspect, the present invention further includes monoclonal and polyclonal antibodies specific for CART protein and DNA, i.e., capable of binding to a CART protein or nucleic acid molecule, as well as hybridoma cell line capable of producing such an antibody.

In other aspects, the invention includes the use of antibodies specifically directed to CART protein or nucleotides, such as to isolate CART protein from sources producing the protein, for purposes of determining the presence or amount of CART protein in a sample, and for other purposes apparent to those skilled in the art.

This invention further includes a method of diagnosis of the presence and location of an CART protein expressing cell using labeled nucleotide probe sequences or labeled antibodies of the invention.

In accordance with these and other aspects of the present invention, CART mRNA was initially identified using the differential display PCR technique of Liang et al., supra. In the differential display PCR techniques, the general strategy is to amplify partial cDNA sequences from subsets of mRNAs by reverse transcription and the polymerase chain reaction (PCR). These short sequences are then displayed on a sequencing gel. Pairs of primers are selected so that each will amplify DNA from about 50 to 100 mRNAs because this number is optimal for display on the gel.

Selection of 3' primers takes advantage of the polyadenylate [poly(A)] tail present on most eukaryotic mRNAs to anchor the primer rate at the 3' end of the mRNA, plus two additional 3' bases. A primer such as 5'T$_{11}$CA allows anchored annealing to mRNAs containing TG located just upstream of their poly(A) tails. By probability this primer will recognize one-twelfth of the total mRNA population because there are 12 different combinations of the last two 3' bases, omitting T as the penultimate base. The primer permits initiation of reverse transcription of only this subpopulation.

Any reverse transcribed cDNA species is amplified by PCR if the distance at which a second primer anneals is smaller than 2 to 3 kb from the beginning of the poly(A) tail. Ideally this annealing position is within 500 bp because cDNAs up to 500 bp can be resolved by size on a DNA sequencing gel. For a 5' primer of arbitrary base sequence, annealing positions to cDNAs should be randomly distributed in distance from poly(A) tail. Therefore, the amplified products from various mRNAs will differ in size. After these PCR products have been labeled with [α-$^{35}$S]-labeled deoxyadenosine triphosphate (dATP), they are displayed by autoradiography as a ladder on a sequencing gel.

The 5' primer should in theory be short, 9 to 11 bp, for it to anneal fairly frequently within a cDNA strand. To permit such short primers to give specific DNA amplification by PCR, PCR parameters are chosen that are optimal for product yield and specificity, such as 40° C. annealing (to allow for some mismatch to occur) and a 30 sec elongation time that allows amplification of short products that can be resolved by a DNA sequencing gel.

PCR generated cDNA representing an mRNA is then recovered from a dried DNA sequencing gel and reamplified with PCR. A DNA band from the sequencing gel is eluted and precipitated to remove contaminants such as urea. The recovered DNA is reamplified in the presence of 20 μM dNTP. The subsequent reamplified PCR DNA is then subcloned and used as a probe for further analysis.

To determine the usefulness of PCR differential display as an approach by which to identify cocaine and amphetamine regulated transcripts, the efficacy of the technique was evaluated by utilizing c-fos specific oligonucleotides capable of generating a PCR product from the rat c-fos transcript (Curran et al., "Isolation and Characterization of the c-fos(rat) cDNA and Analysis of Post-translational Modification in vitro," Oncogene, 2:79–84 (1987)). The observed profile of radiolabeled PCR products showed, as expected, that multiple species of mRNA within the rat cerebellum, striatum and hippocampus can serve as a hybridization target for the two oligonucleotides utilized. A typical reaction generated 50–200 distinct radiolabeled PCR products between 50 and 600 bases in length. Furthermore, the overwhelming majority of PCR products were present at identical levels in these three brain regions isolated from saline, cocaine and amphetamine treated animals. The PCR product representing the c-fos transcript was, however, clearly induced in the striatum and cerebellum from cocaine and amphetamine treated animals, with no such induction observed in the hippocampus. The relative levels of the c-fos PCR products were determined by semi-quantitative densitometric analysis, and the degree of induction was nearly identical to that determined previously by Northern blot analysis. Thus, not only is PCR differential display capable of detecting qualitative differences in relative mRNA levels, but is semi-quantitative as well under the PCR conditions employed.

PCR differential display allows for the microanalysis of transcriptional changes occurring in a given cell or tissue (Liang and Pardee, supra; Liang et al., supra; Bauer et al., supra). In accordance with the present invention, brain (striatum, cerebellum and hippocampus) transcripts were identified whose relative levels are regulated following acute administration of the psychomotor stimulants, cocaine and amphetamine. 96 individual PCR differential display reactions were performed using 12 different 3' primers and 8 different 5' primers. Over 12,000 PCR products were generated, and less than 0.05% of the observed bands exhibited profiles indicative of transcriptional regulation by cocaine or amphetamine. Thus, acute psychomotor stimulant administration appears to affect transcription of an extremely limited array of genes within the brain structures examined, and clearly does not induce wholesale transcriptional effects within the 60 minute time frame examined.

One PCR product from rat brain was identified which represents an mRNA doublet whose relative striatal levels are increased 4- to 5-fold by both acute cocaine and amphetamine treatment. This observation led to the investigation of the effects of another addictive drug, morphine, on transcriptional expression in various rat brain regions. Acute morphine (10 mg/kg, with animals sacrificed 60 minutes following injection) had no apparent effect on RNA doublet levels within the striatum, cortex, hypothalamus, hindbrain, midbrain or hippocampus. Chronic morphine administration (one 75 mg morphine pellet implanted daily for 7 days), and naloxone-precipitated morphine withdrawal (60 minutes post 0.1, 1 and 100 mg/kg naloxone administration) also had no observable effect on RNA doublet levels. Thus, modulation of the catecholaminergic system appears to control RNA doublet levels in the striatum only, with modulation of the opioid system having no observable effect on neuronal transcription.

cDNA sequence analysis characterized the rat mRNA corresponding to the striatal, psychomotor stimulant regulated PCR product. The complete rat cDNA is shown as SEQ ID No.:3. At least two distinct transcriptional events occur in a differential fashion to generate multiple species of mRNA from a unique primary transcript. One such event involves differential poly(A) site utilization. The poly(A) addition event presumably occurs approximately equally at the two AATAAA sites noted in FIG. 1B, as transcriptionally active tissues contain nearly equivalent levels of the 700 and 900 base transcripts. As shown in FIG. 2A–2B the corresponding human transcript is present as a single 900 base species, suggesting that the upstream poly(A) addition site is either not present or not utilized within the primary human transcript. Differential exon splicing in the rat transcript represents a second type of transcriptional event producing multiple species of mRNA. Unlike differential poly(A) site utilization, this event is predicted to effect the ultimate translation product, as the alternately spliced 39 base sequence element is located within the putative protein coding region. Approximately two thirds (11 out of 16) of the rat cDNA clones examined which span the region did not contain the 39 base pair sequence, whereas approximately one third (5 of 16) of the rat cDNA clones examined which span this region contained the 39 bp insert. The rat CART DNA which does not contain the 39 bp insert is hereinafter referred to as rCART1 DNA, whereas the rat CART DNA containing the 39 bp insert is hereinafter referred to as rCART2 DNA. Also, Northern blot analysis of rat midbrain and hypothalamic total RNA using a radiolabeled oligonucleotide complementary to the 39 bp insert showed that the sequence element is present in both the 700 and 900 base transcripts in both tissues. Thus, nuclear factors which determine apparent alternate splicing do not appear to be coupled to events determining poly(A) site utilization.

Northern blot analysis identified the rat brain regions and peripheral tissues which express the RNA doublet. A limited profile of expression was observed, with the hypothalamus and pituitary representing the major sites of transcriptional expression. The midbrain/thalamus and eye also contained relatively abundant levels of the RNA doublet. Other brain regions, as well as the adrenal, contained small yet detectable levels of the transcript. This pattern of expression is suggestive of a potential functional role of the predicted protein product within the neuroendocrine system. Expression within human brain was qualitatively similar to that observed for rat, indicating that the protein product also plays a functional role across mammalian species. Lastly, the use of both sense and antisense strand-specific RNA probes in Northern blot analysis revealed that only one strand of the corresponding gene is transcribed; no hybridization signals were observed in any RNA sample tested when the sense RNA was used as a hybridization probe.

Distribution of the RNA doublet throughout the rat brain as shown by in situ hybridization was predominantly confined to hypothalamic neuroendocrine neurons and limbic neural circuits. Contributions from structures in sexual circuits and those involved in autonomic functions also exist. This unique brain distribution may provide some insights into a possible functional role for the encoded protein product. For example, expression of the RNA doublet is robust in the hypothalamus. Its abundance in this brain region is due, in part, to expression within neuroendocrine neurons such as the paraventricular, arcuate and supraoptic nuclei. Many neurons within these regions send afferents to, and release neuropeptides which modulate pituitary hormone secretion and regulate osmolality (Simerly, "Anatomical Substrates of Hypothalamic Integration." In *The Rat Nervous System*. (Paxinos, Ed.), in press, Academic, New York, N.Y. (1994)). Thus, localization of high levels of the RNA doublet to these neurons, coupled with the predicted structure of the encoded protein product(s) suggest that the transcript may encode a neuroendocrine secretogogue.

Another possible role for the encoded protein is suggested by expression of the RNA doublet in rat limbic neural circuits. For example, the transcript is present within the amygdaloid complex, dentate gyrus of the hippocampus, and the hypothalamic mammillary nucleus and supramammillary nucleus. Expression within the neostriatum is unique by its confinement to the nucleus accumbens and relative absence from the caudoputamen. The nucleus accumbens mediates the reinforcing and rewarding properties of drugs of abuse (Koob, "Drugs of Abuse: Anatomy, Pharmacology and Function of Reward Pathways," *Trends Neurosci.*, 13:177–184 (1992)). Furthermore, the striatum is the only brain region that exhibited up-regulation of rat RNA doublet levels following acute cocaine and amphetamine administration. Such a limited pattern of expression throughout neostriatal, hypothalamic and amygdaloid components of the limbic neural circuits suggest a possible role in reward processes and affect.

The remaining areas of the rat brain exhibiting RNA doublet expression are limited, yet may provide additional information regarding function of the protein. For example, moderate levels of expression are seen in two nuclei which represent major sexual neural circuits - the ventral premammillary nucleus of the hypothalamus, and the posterior dorsal aspect of the medial nucleus of the amygdala (which receives afferents from the former structure). The ventral premammillary nucleus receives inputs from sexually dimorphic brain regions and has been implicated in mediating reproductive behavior and physiology as well as aggressive behavior (Simerly, supra). Rat RNA doublet expression is also observed within sites that modulate autonomic functions. Neurons of the nucleus solitary tract and inferior olive contain moderate to weak levels of the RNA doublet. Noradrenergic neurons of the brainstem such as the locus coeruleus and cells within the Al/Cl region of the ventrolateral medulla express the transcript. The locus coeruleus projects extensively throughout the brain and spinal cord and participates in arousal states (Aston-Jones et al., "Anatomy and Physiology of the Locus Coeruleus Neurons: Functional Implications," In *Norepinephrine: Frontiers in Clinical Science* (Ziegler and Lake, Eds.), Williams and Wilkins, Baltimore, Md., pp. 92–116 (1984)).

As shown in FIG. 1A–1B rat cDNA sequence analysis predicts the translation of a protein either 129 (SEQ ID No.:4) or 116 (SEQ ID No.:6) amino acids in length, depending on the presence or absence of the 39 base in-frame sequence element. Furthermore, polysome analysis indicates that the RNA doublet is efficiently and actively translated in the hypothalamus in vivo, with in vitro translation resulting in the generation of protein products whose observed apparent molecular mass correlates with those predicted solely from nucleotide sequence analysis. Additional computer analysis (employing the BLAST alignment program; Altschul et al., "Basic Local Alignment Search Tool," J *Mol. Biol.*, 215:403–410 (1990)) of the predicted proteins against the 113,000 protein sequences contained within the NIH data base revealed no significant homology. The most noteworthy property of the encoded proteins is the presence of a hydrophobic amino terminal domain. Nineteen of the initial 27 residues are hydrophobic, representing the only region of the predicted protein constituting a major hydrophobic domain. Furthermore, the overall structure of this region corresponds to that of a signal peptide motif (Lingappa and Blobel, "Early Events in the Biosynthesis of Secretory and Membrane Proteins: the Signal Hypothesis," *Rec. Prog. Hormone Res.*, 36:451–475 (1980); van Heijne, "The Signal Peptide," *J Membr. Biol.*, 115:195–201 (1990)), and suggests that the protein products are targeted for secretion following synthesis. Another potentially significant observation is the presence of multiple paired basic amino acid residues (RR, KR, RK and KK) located throughout the predicted protein sequence. Such sites represent those recognized by various neuroendocrine protein convertases (Steiner et al., "The New Enzymology of Precursor Processing Endoproteases," *J Biol. Chem.*, 267:23435–23438 (1992)). Thus, the possibility arises that the predicted protein may be a substrate target for post-translation proteolytic cleavage events.

A human hypothalamic cDNA and genomic DNA library were screened with a radiolabeled full-length rat CART cDNA probe under stringent conditions to isolate human CART cDNA and genomic clones. The full length human cDNA sequence (SEQ ID No.:7) is approximately 800 bases in length, excluding the poly(A) tail which was present on several cDNA clones. Although three poly(A) addition recognition sites (AATAAA) are present within the 3' untranslated region, cDNA clone analysis coupled with Northern blot studies indicate that only one is predominantly utilized in vivo. This is in contrast to the rat CART transcript, where two poly(A) sites are recognized at an apparently equal frequency in vivo, resulting in the presence of a distinct RNA doublet following Northern analysis (Douglass et al., "PCR Differential Display Identifies a Rat Brain mRNA That is Transcriptionally Regulated by Cocaine and Amphetamine," *J Neurosci.*, 15:2471–2481 (1995). Nucleotide sequence comparison to full length rat CART cDNA reveals an overall identity of approximately 80%, with a 92% degree of homology observed within the predicted protein coding region. The majority of the latter differences are at third base codon locations.

Comparison of the human cDNA sequence (SEQ ID No.:7) to that of the genomic DNA (SEQ ID No.:9) reveals that mature human CART mRNA is encoded by three distinct exons. The two resulting introns are relatively small (approximately 425 and 540 bp in length) and are located within the presumed CART protein coding region. In the 5' gene flanking region a consensus TATAAA box is observed at position −31, indicative of a functional promoter element, while in the 3' flanking region the genomic DNA sequence diverges from the cDNA sequence at the site of poly(A) addition, as expected.

Analysis of human CART genomic DNA also reveals the apparent molecular basis for an alternate splicing event which occurs in the rat CART transcript (see FIG. 3A–3C). In the rat, a 39 base sequence is present in approximately one-third of the mature CART transcripts expressed in the striatum and hypothalamus as determined by both cDNA sequence and PCR analysis. This sequence, when present, is found within the predicted CART protein coding region, resulting in the presence or absence of a 13 amino acid sequence within the CART protein. Analysis of human CART genomic DNA identifies a highly related 39 base sequence at the 3' end of the first intron (FIG. 3A). 25 of 39 nucleotides are conserved between the two species, with an even lower degree of conservation (6 of 13) observed at the corresponding amino acid level. It is currently unclear as to why this 39 base sequence is alternately spliced in rat brain tissues expressing the CART transcript, while no such event is observed following an identical analysis of human hypothalamic RNA.

Figure 4:
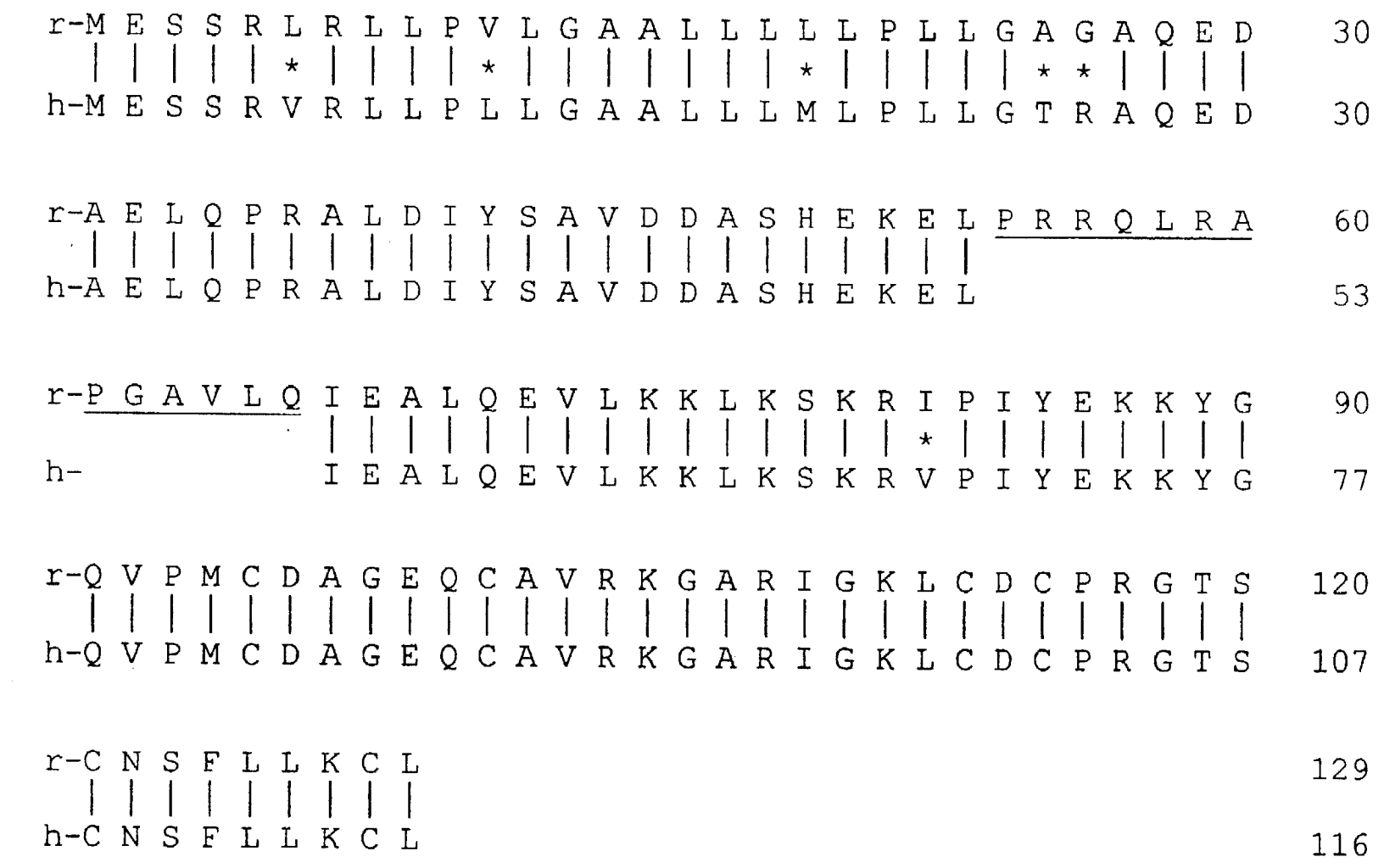

The first potential translation initiation codon is located at nucleotide 20 within human CART cDNA, and the cDNA coding sequence extends to the TGA termination site (*) at nucleotide 368, predicting the generation of a protein 116 amino acid residues in length. The human CART mRNA cap site is located at nucleotide +1 (FIG. 3A). The most noteworthy property of the predicted protein is the presence of an amino terminal hydrophobic domain (27 residues in length) conforming to the motif of a signal peptide (Lingappa and Blobel, supra; von Heijne et al., supra) and suggesting that the protein is targeted for entry into the secretory pathway. The sequence of the predicted human CART protein is 95% identical to that for rCART1 (see FIG. 4). Within the hydrophobic amino terminal domain, three conservative (V6L, L11V, and M19L) and two nonconservative (T25A, and R26G) substitutions are observed. However, throughout the remaining 90 residues only one conservative substitution (V69I) is present. This observation of significant conservation at the amino acid sequence level is consistent with the notion that the CART protein plays a conserved role within the mammalian neuroendocrine system.

The use of hCART DNA and rCART DNA, or fragments thereof, as a probe in the isolation, purification, and study of other CART proteins from other organisms is contemplated. Oligonucleotide fragments of CART DNA can also be used as primers to amplify (with specific DNA polymerases) genomic DNA, isolated, for example, from bacteria, fungi, avian, and mammalian sources. The amplified genomic DNA can then be analyzed to identify sequence variation/abnormality using the polymerase chain reaction assay (Saiki et al., Science 230:1350 (1985). See also, Mullis, K. B., U.S. Pat. No. 4,683,202, Jul. 28, 1987; and Mullis, K. B., U.S. Pat. No. 4,683,195, Jul. 28, 1987).

For the analysis of mRNA for CART, or mRNA for related proteins, dot hybridization and Northern hybridization analyses can be used to characterize mRNA encoding CART protein or CART protein-like molecules quantitatively and qualitatively. From these studies valuable information can be obtained about the number of different forms of CART genes and their expression in various cell types, e.g., bacteria, fungi, arian, and mammalian.

Thus, in addition to characterization of CART DNA and polypeptides described in detail above, the present invention has the following advantages:

(1) The nucleic acids coding for rCART or hCART can be used as probes to isolate other members of the CART gene family.

(2) The nucleic acids coding for rCART or hCART can be used to derive oligonucleotide probes to determine the presence of CART mRNA and the expression of CART and other CART genes in various tissue types.

(3) rCART or hCART nucleotide sequences can be used to predict the primary amino acid sequence of the protein for production of synthetic peptides.

(4) Synthetic peptides derived from the above sequences can be used to produce sequence-specific antibodies and antibody fragments.

(5) Immunoassays for CART polypeptides can be produced with these sequence-specific antibodies and synthetic peptides.

(6) The aforementioned immunoassays can be used as diagnostics for cocaine or amphetamine usage, and/or for susceptibility or predisposition to cocaine or amphetamine addiction.

Peptides according to the present invention can be labelled by conventional means using radioactive moieties (e.g., $^{125}I$), enzymes, dyes, fluorescent compounds, and other conventional labels. Several possible configurations for immunoassays according to the present invention can be used. The readout systems capable of being employed in these assays are numerous and non-limiting examples of such systems include fluorescent and colorimetric enzyme systems, radioisotopic labelling and detection and chemiluminescent systems. Two illustrative examples of immunoassay methods are as follows:

(1) An enzyme linked immunoassay (ELISA) using an antibody preparation according to the present invention (including Fab or F(ab)' fragments derived therefrom). To a solid phase (such as a microtiter plate or latex beads) is attached a purified antibody or antibody fragment having a specificity for CART polypeptides. This solid phase antibody is contacted with the sample containing CART. After washing, the solid phase antibody-antigen complex is contacted with an enzyme-conjugated anti-peptide antibody (or conjugated fragment) having a CART binding specificity different from that of the solid phase antibody. After washing away unbound conjugate, color or fluorescence is developed by adding a chromogenic or fluorogenic substrate for the enzyme. The amount of color or fluorescence developed is proportional to the amount of CART in the sample.

(2) A competitive fluorometric immunoassay using fluorescently labelled peptide or synthetic peptides of the sequences for CART polypeptides. In this example, the purified peptide expressed by cells or synthetic peptides thereof are fluorescently labelled. To a solid phase is attached a purified antibody having a binding specificity for CART polypeptides. This solid phase is then contacted with sample containing CART polypeptide to which has been added fluorescent peptide probe. After binding, excess probe is washed away and the amount of bound probe is quantitated. The amount of bound fluorescent probe will be inversely proportional to the amount of CART polypeptide in the sample.

In the nucleic acid hybridization method according to the present invention, the nucleic acid probe is conjugated with a label, for example, an enzyme, a florophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods of these last two techniques are described by Gillespie and Bresser, "mRNA Immobilization in NaI: Quick Blots," *Biotechniques*, 184–192, (November/December 1983) and Lawrence and Singer, "Intracellular Localization of Messenger RNAs for Cytosketal Proteins," *Cell* 45:407–415 (1986), respectively. The readout systems can be the same as described above, e.g., enzyme labelling, radiolabelling, etc.

The foregoing and other aspects of the invention may be better understood in connection with the following examples, which are presented for purposes of illustration and not by way of limitation.

EXAMPLES

Example 1

Differential Display of Rat CART-RNA

Adult 90-day old male Sprague-Dawley rats were kept under a 12 hr light/12 hr dark cycle and given food and water ad libitum. A single dose of cocaine (20 mg/kg) dissolved in saline, amphetamine (6 mg/kg) dissolved in saline or saline alone (as control) was given intraperitoneal (i.p.) to each of 6–10 rats. The animals were sacrificed 1 hr after injection via halothane anesthetization to unconsciousness (<1 min) and decapitation. The whole brain was removed and rinsed in ice-cold PBS for 1 minute prior to dissection. Cerebellum, striatum and hippocampus were dissected and immediately stored on dry ice at −70° C.

Brain dissections were performed as described (Glowinski and Iversen, "Regional Studies of Catecholamine in the Rat Brain: The Disposition of [$^3$H] norepinephrine, [$^3$H]dopamine, and [$^3$H]DOPA in Various Regions of the Brain," *J Neurochem.*, 13:665–669 (1966)). Total RNA from the aforementioned brain regions (plus additional brain regions) and peripheral tissues was immediately prepared using a modified acid phenol technique (Chomczynski and Sacchi, "Single-Step Method of RNA Isolation by Acid Quanidinium Thiocyanate-Phenol-Chloroform Extraction," *Anal. Biochem.*, 162:156–159 (1987)), with final concentration determined spectrophotometrically.

Following the determination of concentration, RNAs from the cerebellum, striatum and hippocampus were pooled from 6 to 10 animals receiving either the saline, cocaine or amphetamine injections. Reverse transcription was performed essentially as described previously (Liang and Pardee, supra) using $T_{11}VN$ oligonucleotides as primers. The only significant modification involved a primer preannealing step at 35° C. for 60 minutes prior to initiation of reverse transcription by the addition of dNTPs and MMLV reverse transcriptase. Reverse transcription reactions were then subjected to PCR in the presence of $^{35}S$-α-dATP and oligonucleotides specifically designed for differential display (Liang and Pardee, supra). Final concentrations of 1 mM $MgCl_2$ and 20 µM dNTPs were found to be optimal for these two reagents. The 5' PCR oligonucleotide (10 mer, 50% G/C content, ACGTCTCATG, SEQ ID No.:1) was present at a final concentration of 0.5 pmol/µl, while the 3' PCR oligonucleotide (TTTTTTTTTTGC, SEQ ID No.:2) was present at a final concentration of 2.4 pmol/µl. PCR conditions employing a Perkin Elmer Cetus GeneAmp PCR System 9600 thermocycler were: 40 cycles of denaturation at 94° C. for 30 sec, primer annealing at 40° C. for 120 sec, and extension at 72° C. for 30 sec. A final extension reaction was then performed at 72° C. for 7 min. Radiolabeled reaction products were subjected to high resolution polyacrylamide/urea gel electrophoresis as described (Liang and Pardee, supra). The relative abundance of an approximately 400 bp PCR product was significantly increased in striatal RNA samples from animals treated acutely with cocaine or amphetamine. No such drug induced increase was observed for the hippocampal RNA samples, and no PCR product was observed in the cerebellar RNA samples regardless of drug treatment. To further characterize this PCR product, the fragment was isolated from a preparative acrylamide/urea gel, subjected to PCR under standard conditions, and subcloned into the pCRII vector (Invitrogen, San Diego, Calif.) via the T/A cloning procedure. Inserts were analyzed by supercoil dideoxynucleotide sequencing.

To confirm that the cloned PCR product represents a striatal mRNA which is transcriptionally regulated by psychomotor stimulants, the purified DNA fragment was radiolabelled to serve as a hybridization probe for Northern blot analysis. For Northern blot analysis, total RNA (3–5 µg) was separated by electrophoresis on 6% formaldehyde/1.2% agarose gels. The RNA was transferred to Magna NT nylon membranes (Micron Separations Inc., Westboro, Mass.) by capillary action with 20×SSC, followed by UV crosslinking. The membranes were then briefly dipped in 0.3 M sodium acetate, 0.02% methylene blue to stain the transferred RNA. 28S and 18S rRNA were readily apparent, and served as a means by which to standardize for the amount of RNA contained within each sample. Following removal of stain by boiling in water for 10 min, the membranes were prehybridized for 3–24 hr at 60° C. in hybridization buffer (5% SDS, 400 mM sodium phosphate (7.0), 1 mM EDTA, 1 mg/mil BSA (fraction V) and 50% formamide). The prehybridization buffer was discarded and replaced with fresh hybridization buffer including the hybridization probe. Hybridization proceeded for 16–24 hr at 42° C. Membranes were subsequently washed with 1% SDS, 0.5×SSC and 1 mM EDTA at 50°–55° C. for 1–4 hr. After washing, membranes were exposed multiple times to Kodak XAR-5 film in order to obtain a range of hybridization signal intensities for semi-quantitative densitometric analysis. For each RNA sample, autoradiographic signals within the linear range of film sensitivity were digitized using an X-Ray Scanner Corp. model MSF300ZS laser scanner and Adobe Photoshop XSF software. Relative intensities were quantified using Image software. RNA doublet signal intensities were standardized against 28S or 18S rRNA (detected by methylene blue staining), or cyclophilin mRNA (detected by Northern blot analysis employing radiolabeled cRNA as a hybridization probe). In striatal and hippocampal RNA isolated from saline injected animals, two hybridization positive transcripts were observed which are approximately 700 and 900 bases in length. In the striatum, cocaine and amphetamine treatment increased the relative level of the RNA doublet by 4- to 5-fold, while no such modulation was observed in the hippocampus. Additional Northern blot analysis of RNA isolated from hypothalamus, midbrain/ thalamus, hindbrain and cortex also showed no transcriptional regulation by acute cocaine or amphetamine treatment. No RNA doublet was observed in cerebellar RNA samples regardless of treatment. Thus, the profile of this RNA within the cerebellum, striatum and hippocampus as determined by Northern blot analysis conforms to that for the corresponding PCR product identified by differential display analysis.

Example 2

Isolation and Cloning of Rat CART cDNA

Following confirmation that the PCR product from Example 1 was derived from a psychomotor stimulant regulated transcript, rat striatal and hypothalamic cDNA libraries were screened under stringent hybridization conditions utilizing the radiolabelled PCR fragment as a hybridization probe. Specifically, cDNA clones were isolated from rat striatal and hypothalamic libraries in the lambda vector, ZAPII (libraries purchased from Stratagene, La Jolla, Calif.). Approximately $5 \times 10^5$ clones were plated from each of the aforementioned libraries, and screened under stringent hybridization conditions employing the radiolabeled PCR fragment as a hybridization probe. About 20 distinct hybridization positive clones were plaque purified, the cDNA inserts isolated in phagemid form following superinfection with helper phage, and the inserts sequenced as described above. Subsequent nucleotide sequence analysis was performed employing the Wisconsin CGC suite of analytical software. The nucleotide sequence of the full length cDNA has been assigned accession number U10071 in the GenBank database. 5' RACE was also used to isolate cDNA/ PCR products representing the 5' end of the mRNA. The rat cDNA sequence (SEQ ID No.:3) representing the approximately 900 base transcript is shown in FIG. 1A–1B. The cDNA is 840 bases in length, excluding an $(A)_{26}$ tail. The poly(A) addition recognition sequence, AATAAA, at position 814 directs poly(A) tail addition at this site. A second species of cDNA clone contained an $(A)_{40}$ tail following nucleotide 579, utilizing the AATAAA element at position 548, to produce an approximately 700 base transcript. Thus, the molecular mechanism underlying the appearance of the RNA doublet appears to be differential poly(A) site utilization. cDNA nucleotide sequence analysis also uncovered an apparent alternate exon splicing event within the predicted translated region of the RNA. Approximately one third of the cDNA clones sequenced contained the 39 nucleotides representing those from 179–217, while the remaining clones did not. Lastly, nucleotides 158 and 556 represent the 5' ends of the two oligonucleotides used in the original PCR differential display analysis. Several mismatches are present between the PCR differential display oligonucleotides and the complementary cDNA sequence, as anticipated. The predicted translational reading frame begins with an ATG at nucleotide 20 and extends to the TGA termination site at nucleotide 407. An arrow in FIG. 1B denotes the carboxy-terminal residue of the predicted hydrophobic signal sequence. The sequence of the original PCR differential display fragment also matches that located between nucleotides 168 and 543 in the cDNA clones.

As described above, the first potential translation initiation codon is located at nucleotide 20. In 90–95% of the vertebrate transcripts analyzed, the first 5' AUG represents the site for translation initiation (Kozak, "The Scanning Model for Translation: An Update," *J. Cell Biol.*, 108:229–241 (1989)). Furthermore, the nucleotide sequence in which this ATG is embedded is similar to that representing a consensus Kozak translation initiation sequence element (GCCGCCRCC<u>ATG</u>G) (SEQ ID NO.:14). The predicted encoded polypeptide is either 129 or 116 residues in length, depending on the presence or absence of nucleotides 179–217 within the putative protein coding region, respectively. The first 27 residues represent an amino terminal hydrophobic domain conforming to the motif of a signal peptide (Lingappa and Blobel, supra; van Heijne, supra), suggesting that the polypeptide may be targeted for entry into the secretory pathway. There are also multiple paired basic amino acid residues located throughout the molecule which could theoretically serve as target sites for post-translation proteolytic cleavage events (Steiner et al., supra). One such site is present within the alternately spliced domain encoding residues 54–66, further suggesting that if proteolytic cleavage events did occur, then different peptide end products would be produced from the two distinct primary translation products.

Example 3

Distribution of Rat CART RNA Within the Adult Rat Brain and Peripheral Tissues

For in situ hybridization analysis of rat brain, a slightly modified version of the Simmons et al., "A Complete Protocol for in situ Hybridization of Messenger RNAs in Brain and Other Tissues With Radiolabelled Single-Stranded RNA Probes," *J Histotechnol*, 12:169–181 (1989) protocol was used. Serial sections 30 µm thick from three adult male Sprague-Dawley rat brains were cut on a sliding microtome. Whole brain series were collected from prefrontal cortex to the cervical spinal cord, and each section in a series was approximately 270 µm from an adjacent section. Free floating sections were stored in cryoprotectant (50% 0.05 M sodium phosphate buffer, pH 7.3, 30% ethylene glycol, 20% glycerol) at −20° C. for 2–6 weeks. Sections were then mounted onto subbed and poly-L-lysine coated slides after 3 washes (in 0.05 M sodium phosphate buffer, pH 7.3), vacuum dried, and stored desiccated at −70° C. until hybridization. Hybridization with a near full length rCART $^{35}$S-α-UTP radiolabeled antisense cRNA probe was performed at 63° C., with the most stringent post-hybridization wash step performed at 75° C. Hybridization with a sense RNA probe served as a control for in situ signal specificity. Slides were exposed to CRONEX film (Amersham) for 2 days. They were then dipped in NB-20 emulsion (Kodak) and developed 5 days thereafter.

To identify specific neuroanatomical structures, adjacent sections were Nissl stained followed by microscopic evaluation. The rat brain atlas of Swanson, "Brain Maps: Structure of the Rat Brain," Elsevier, New York, N.Y. (1992), was used to identify specific in situ hybridization positive cells and brain nuclei, as well as providing a nomenclature for subsequent labeling.

Analysis of relative rCART RNA levels within gross brain structures and peripheral tissues was carried out by Northern blot analysis with an antisense cRNA probe following subcloning of the rCART cDNA fragment representing nucleotides 42–800 into the plasmid pBSII SK– (Stratagene). A 650 bp fragment (35-685, PstI/HincII) of rat cyclophilin cDNA was also subcloned into pGEM 3Z, with relative cyclophilin mRNA levels serving as internal controls. Radiolabelled ($^{32}$P-α-UTP) RNA probes were synthesized in vitro using either SP6, T3 or T7 RNA polymerase. Specific activities of cRNA probes were routinely greater than $3\times10^9$ cpm/μg plasmid.

The major site of synthesis of the CART RNA is the hypothalamus. Relatively abundant RNA levels were also observed in the thalamus/midbrain, with significantly lower expression observed in the cortex, striatum, hippocampus and hindbrain. Semi-quantitative densitometric analysis of the hybridization signals revealed that hypothalamic CART RNA levels are approximately 300-fold greater, and midbrain/thamus RNA levels 10-fold greater than striatal levels. Analysis of RNA isolated from peripheral tissues also detected the presence of the CART RNA in rat eye and adrenal, while no hybridization signal was observed in the other 13 tissues examined. Levels of the CART RNA in the eye approximated those of the midbrain/thalamus, while adrenal levels are similar to those observed in the striatum. Several additional endocrine tissues were also evaluated for expression of the CART mRNA. No hybridization signal was observed in rat ovary and uterus RNA. However, a robust hybridization signal was observed when pituitary RNA was examined; the relative intensity of the pituitary hybridization signal approximates that observed for the hypothalamus. Expression of the CART RNA is thus limited to neuroendocrine tissues, with dramatically varied levels of transcriptional expression observed throughout the brain.

Further Northern blot analysis also confirmed that the CART transcript is present in RNA isolated from human brain. Relatively abundant levels of an approximately 900 base hybridizing transcript were observed in RNA from human hypothalamus, frontal cortex and midbrain, with lower levels seen in the hippocampus, motor cortex and striatum. No such hybridization signal was observed in cerebellar RNA. Thus, the pattern of distribution of the transcript in human brain was relatively conserved to that observed for rat brain. However, only a single species of hybridizing RNA was present in human, in contrast to the doublet RNA band which was consistently observed in rat.

Regional expression of the CART RNA throughout the adult rat brain was more precisely determined by in situ histochemical analysis. For these studies a 790 base cRNA hybridization probe spanning the putative coding region (including the alternately spliced 39 base insert) and 3' noncoding region was utilized. The most intense hybridization signals were observed in the Edinger-Westphal nucleus and induseum griseum. Major expression was also seen in the periventricular zone of the hypothalamus (especially the paraventricular and arcuate nuclei) and cells throughout the medial hypothalamus (typified by labeling of the supraoptic nucleus and peri-fornical region). Within these structures, intense hybridization signals were observed at the single cell level.

Telencephalic hybridization signals were limited to a few areas. Of note was the distribution in the neostriatum where moderate labeling was evident in the ventral region, consisting of the nucleus accumbens and olfactory tubercle. This area of hybridization positive cells stretched along the nucleus accumbens border within striosomes of the ventrolateral caudoputamen. Within the neocortex, moderate labeling was seen only in the primary somatosensory area (layer 4) and the piriform area. Intense labeling was observed in the induseum griseum, with the bed nuclei of the stria terminalis and the dorsal blade of the dentate gyrus of the rostral hippocampus exhibiting moderate to weak labeling. Moderately intense hybridization signals were also seen in the amygdaloid complex, particularly in the medial part of the septal nucleus, posterior dorsal part of the medial nucleus, posterior cortical nucleus, and posterior basolateral nucleus.

In the diencephalon, the hypothalamus exhibited the most extensive labeling distribution of any brain region examined. Intense to moderate labeling of cells was evident throughout entire nuclei such as the paraventricular (particularly the parvocellular region), arcuate and supraoptic nuclei. Moderate labeling was seen in the posterior periventricular nucleus, ventral and medial premammillary nucleus, and lateral aspect of the supermammillary nucleus. Scattered cells in the peri-fornical region, lateral hypothalamus, and posterior hypothalamus exhibited intense to moderate signals. Within the thalamus, the medial aspect of the zona incerta, ventral half of nucleus reuniens, and lateral habenula were the only structures exhibiting moderate to weakly intense hybridization signals.

The mesencephalon contained the fewest number of hybridization positive cells. However, within this region the Edinger-Westphal nucleus exhibited intense labeling. Scattered cells with moderate to weak labeling were also noted in the dorsal periaqueductal gray. The rhombencephalon also contained regions of hybridization positive cells. Both the inferior olive and nucleus of the solitary tract exhibited moderate labeling, where as the locus coeruleus and nucleus incertus showed weak labeling. Scattered cells throughout the Al/Cl region of the nucleus ambiguus further exhibited moderate labeling.

Hybridization of all aforementioned brain sections with a sense CART cRNA probe under identical conditions showed no labeling of any of the structures described above. Thus, the hybridization signals which were observed employing the antisense cRNA probe were specific, and represented cells expressing the CART RNA.

Example 4

Isolation and Characterization of Human CART cDNA and Genomic DNA

A human hypothalamic cDNA and genomic DNA library were screened with a radiolabeled, full-length rat CART cDNA probe under stringent hybridization conditions to isolate human CART cDNA and genomic DNA clones. cDNA clones were isolated from a human hypothalamic cDNA library in the lambda vector ZAPII (library #77425, obtained from ATCC, Rockville, Md.). Genomic clones were isolated from a human genomic DNA library in the lambda vector Charon 4A (library #37385, also obtained from ATCC). Approximately $5\times10^6$ clones were plated from each of the aforementioned libraries, and screened under stringent hybridization conditions employing radiolabeled full-length rat CART cDNA as a hybridization probe.

Hybridization positive cDNA clones were plaque purified, the cDNA inserts isolated in phagemid form following superinfection with helper phage, and the inserts subjected to complete nucleotide sequence analysis. The 5' end of human CART cDNA was determined by 5' RACE (GIBCO-BRL, Gaithersburg, Md.). Briefly, human hypothalamic poly (A+) mRNA was incubated with a complementary oligonucleotide to prime first strand cDNA synthesis. The cDNA products were then tailed with terminal deoxytransferase and dCTP, and subjected to PCR with appropriate oligonucleotides. The resulting cDNA fragments were subcloned and subjected to full nucleotide sequence analysis.

For genomic DNA analysis, hybridization positive genomic DNA clones were plaque purified, and phage DNA isolated. Eight unique oligonucleotides spanning the entire human CART cDNA sequence were then utilized as hybridization probes for Southern blot analysis of the cloned genomic DNA fragments. A 2.5 kb SmaI/EcoRI genomic DNA fragment was shown to contain the entire CART mRNA sequence following this analysis, and was subsequently subjected to complete nucleotide sequence analysis following the subcloning of appropriate, smaller DNA fragments into M13 vectors, resulting in the complete sequence shown in SEQ ID No.:9. All nucleotide sequence analysis was performed employing the Wisconsin CGC suite of analytical software. The nucleotide sequence of full length human CART cDNA has been assigned accession number U16826 in the GenBank database, with the human CART gene sequence assigned accession number U20325.

PCR/Southern blot analysis of DNA isolated from 24 human/rodent somatic cell hybrids retaining one or two human chromosomes was used to localize the human CART gene to a specific chromosome. DNA was analyzed from NIGMS human/rodent somatic cell hybrid mapping panel #2. Included in the panel was genomic DNA isolated from the human cell line IMR-91, the hamster cell line RJK88, and the mouse cell line 3T6. PCR was performed on all DNA samples using oligonucleotides directed against unique sequences found in the 3' untranslated region of human CART mRNA (5' oligo to nucleotides 381-405, and 3' oligo to nucleotides 613-637, generating a PCR fragment 256 bp in length). The resulting PCR reactions were then subjected to 1.5% agarose gel electrophoresis and Southern blot analysis employing full length, $^{32}$P-radiolabeled human CART cRNA as a hybridization probe. The presence of a hybridization-positive, 256 bp PCR-generated product indicates the presence of human genomic DNA encoding the CART transcript. Authenticity of this hybridization signal was further shown by demonstrating that its appearance is dependent on the presence of both 5' and 3' oligonucleotides in the original PCR reaction. The oligonucleotides employed for PCR reactions were directed against sequences found in the 3' untranslated region of human CART mRNA (5' oligo to nucleotides 381-405, and 3' oligo to nucleotides 613-637, generating a PCR fragment 256 bp in length). mRNA untranslated regions are rarely conserved to a high degree between species, and for the aforementioned oligonucleotides this is clearly the case. A hybridization-positive, PCR-generated DNA fragment of appropriate size was observed only with the human genomic DNA sample, with no such signal observed for the corresponding murine and hamster DNA sample. Furthermore, generation of the human genomic DNA signal was dependent on the presence of both 5' and 3' PCR oligonucleotides, supporting the authenticity of the amplified DNA fragment. A similar hybridization signal was observed only in the human/rodent somatic cell hybrid sample containing human chromosome 5. No such signal was observed for the other 23 DNA samples tested, and generation of the signal was also dependent upon the use of both 5' and 3' oligonucleotides in the PCR reaction. An identical analysis was performed on DNA from a different panel of human/rodent somatic cell hybrids, and confirmed localization of the human CART gene to chromosome 5.

Example 5

Northern Blot Analysis of Human Brain Total RNA

Within the adult male rat, CART mRNA is present exclusively in neural and endocrine tissues, as described above. Northern blot analysis revealed that in the rodent brain, CART mRNA levels are highest within the hypothalamus, with midbrain/thalamus also exhibiting moderate levels of expression. Lower CART mRNA levels are also observed in the hindbrain, hippocampus, striatum and cortex. The cerebellum appears to be the only major brain structure devoid of detectable levels of CART mRNA. In situ histochemical analysis further determined that within the aforementioned rodent brain regions, CART mRNA is found within specific neural circuits. For example, numerous limbic neural circuits express the CART transcript, including the amygdaloid complex, dentate gyrus of the hippocampus, hypothalamic mammillary and supramammillary nucleus, and nucleus accumbens. These sites of synthesis suggest a potential functional role in reward processes and affect. Another predominant circuit expressing major levels of the CART transcript is that represented by hypothalamic neuroendocrine neurons, suggesting a role for the CART protein in regulation of endocrine events.

Observation of CART mRNA in similar human brain regions indicated that CART plays a conserved functional role within the mammalian brain. To prove this point, Northern blot analysis was performed on total RNA isolated from various regions of human brain, as follows. Human brain (with a negative drug toxicology profile) RNA (3-5 μg as determined spectrophotometrically) was separated by electrophoresis on a 6% formaldehyde/1.2% agarose gel. The RNA was transferred to a nylon membrane by capillary action with 20×SSC, followed by UV cross-linking. The membranes were then briefly dipped in 0.3 M sodium acetate, 0.02% methylene blue to stain the transferred RNA. 28S and 18S rRNA were readily apparent, and served as a means by which to standardize for the amount of RNA contained within each sample. Following removal of stain by boiling in water for 10 minutes, the membranes were prehybridized for 3-24 hr at 60° C. in hybridization buffer (5% SDS, 400 mM sodium phosphate (7.0), 1 mM EDTA, 1 mg/ml BSA (fraction V) and 50% formamide). The prehybridization buffer was discarded and replaced with fresh hybridization buffer including a full length, $^{32}$P-radiolabeled human CART cRNA probe. Hybridization proceeded for 16-24 hr at 42° C. Membranes were subsequently washed with 1% SDS, 0.05×SSC and 1 mM EDTA at 70°-75° C. for 1-4 hr, followed by exposure to Kodak XAR-5 film.

Rat eye total RNA served as a control sample to document the size of the rat CART mRNA doublet (approximately 900 and 700 bases in length) which resulted from the use of multiple poly(A) recognition sites (AATAAA). For the human brain RNAs examined, a major CART transcript was observed which was approximately 900 bases in length. This length was consistent with the size and sequence of the human CART cDNA clones which were analyzed. Some samples revealed the presence of smaller species of hybridization-positive mRNAs, which may be the result of alternate poly(A) site utilization or RNA degradation. Major sites of synthesis of the human CART transcript were represented by the hypothalamus, frontal cortex and midbrain, with moderate to low levels observed in the hippocampus, motor cortex, and caudate-putamen. No observable CART mRNA was detected in the cerebellum. Thus, the gross pattern of distribution of CART mRNA throughout the human brain is qualitatively similar to that observed for the rat, suggesting that the encoded CART protein plays a conserved functional role across mammalian species.

Example 6

CART Polysome Analysis 0.2 g of adult male Sprague-Dawley rat hypothalamus was homogenized in 2.2 ml HKM buffer (100 mM NaCl, 20 mM Hepes (7.45), 1.5 mM $MgCl_2$, 0.5% Triton X-100, 2 mM vanadyl ribonucleotide complex) at 4° C. 0.2 ml was removed for experimental control purposes and stored at −20° C. The remaining material was centrifuged at 9K rpm for 5 min at 4° C. in an SS34 rotor. The supernatant was removed and vortexed briefly. 1 ml was removed and loaded onto an approximately 11 ml, 10–35% sucrose gradient in 1×HMK buffer. Another 1 ml of supernatant was removed and adjusted to 20 mM EDTA, and likewise loaded onto an approximately 11 ml, 10–35% sucrose gradient in 1×HMK buffer. The two sucrose gradients were then subjected to ultracentrifugation at 37 krpm for 115 min at 4° C. in an SW41 rotor. Following centrifugation, the gradient was fractionated from the top into 1 ml aliquots (approximately 12 fractions were collected). RNA was then extracted from each gradient aliquot (as per procedures routine to our lab), and subjected to Northern blot analysis employing a cRNA probe specific for the detection of rat CART mRNA.

Northern blot analysis was performed as described above. Rat hypothalamic extracts either did not contain (−EDTA), or did contain (+EDTA) EDTA at a final concentration of 20 mM prior to ultracentrifugation. In the gradient not containing EDTA, positive hybridization signals for rat CART mRNA were observed in fractions 8–12, with the majority of the hybridization signals observed in fractions 9–11. This represented gradient fractionated material of a relatively high density, as the material was found in the lower gradient fractions. RNA associated with polysomes is typically localized to this region of a 10–35% sucrose gradient. Thus, this result suggests that in the rat hypothalamus, CART mRNA is found on polysomes and is thus actively translated in vivo.

In the gradient containing EDTA, positive hybridization signals for rat CART mRNA were observed in fractions 2–4, with the majority of the hybridization signals observed in fractions 2 and 3. This represents gradient fractionated material of a relatively low density, as the material is found in the upper gradient fractions. Free RNA is typically localized to this region of a 10–35% sucrose gradient. As the ability of ribosomes to interact with RNA is dependent on $Mg_2$, and EDTA serves to chelate (remove) $Mg_2$ from solutions, this result represents an expected negative control.

Example 7
Production of Rat CART Fusion Proteins in Bacteria pET15-rCART1

Rat CART1 protein was expressed as a fusion protein using the Novagen bacterial expression plasmid, pET15b. The coding region of rat CART1 cDNA (excluding the predicted signal sequence) was amplified by PCR using the following primers:

N-terminal: CGATCGGCATATGCAGGAGGATGCCGAGCTG(SEQ ID No.:10)

C-terminal: CGGCGGATCCGTTAAAGCGGCTCCAGGG(SEQ ID No.:11)

The PCR product was isolated, purified, incubated with appropriate restriction enzymes and ligated into pET 15b, in accordance with the manufacturer's instructions. Ligations were transformed into E. coli, transformants isolated and resulting plasmid DNA analyzed by both restriction analysis and nucleotide sequence analysis. Nucleotide sequence analysis insured that no errors in nucleotide sequence within the rCART1 coding region had occurred during the PCR reaction.

The resulting pET15b-rCART1 fusion protein had the following structure (underlined sequence represents that encoded by pET 15b, with the sequence shown in italics representing rCART1):

MGSSHHHHHHSSGLVPRGSHMQED . . . (rCART1) . . . KCL(SEQ ID No.:15)

where QED . . . (rCART1 ) . . . KCL represents the predicted mature rat CART protein sequence, SEQ ID No.:6 (lacking the 13 amino acid alternatively translated insert SEQ ID No.:5).

The pET15b-rCART1 plasmid was then transformed in E. coli strain BL21 (Novagen) for protein expression. 100 ml LB with 50 µg/ml Amp was inoculated with 0.1 ml of an overnight culture and grown at 37° C. until the OD600 was 0.4–0.6. Samples were removed for SDS gel analysis and cultures were induced with 1 ml 100 mM IPTG. Cultures were incubated for three additional hours at 37° C. Cultures were then harvested by centrifugation, supernatants discarded and the cell pellet stored at −70° C. until fusion protein purification.

pET23b-rCART2 rCART2 was expressed as a fusion protein using the Novagen bacterial expression system plasmid, pET23b. The coding region of rat CART2 cDNA (excluding the predicted signal sequence) was amplified by PCR using the following primers:

N-terminal: GGTCGGGATCCGCAGGAGGATGCCGAGCTG(SEQ ID No.:12)

C-terminal: GGTGCTCGAGCAAGCACTTCAAGAGGAAAG(SEQ ID No.:13)

The PCR product was isolated, purified, incubated with appropriate restriction enzymes and ligated into pET23b. Ligations were transformed into E. coli, transformants isolated and resulting plasmid DNA analyzed by both restriction analysis and nucleotide sequence analysis. Nucleotide sequence analysis insured that no errors in nucleotide sequence within the rCART2 coding region had occurred during the PCR reaction.

The resulting pET23b-rCART2 fusion protein had the following structure (underlined sequence represents that encoded by pET23b, with the sequence shown in italics representing rCART2):

MASMTGGQQMGRDPQED . . . (rCART2) . . . KCLLGHHHHHH(SEQ ID No.:16)

where QED . . . (rCART2) . . . KCL represents the entire rat CART sequence, SEQ ID No.:4, minus the signal sequence.

The pET23b-rCART2 plasmid was then transformed in *E. coli* strain pLysS (Novagen) for protein expression. 100 ml LB with 50 µg/ml Amp and 34 µg/ml chloramphenicol was inoculated with 0.1 ml of an overnight culture and grown at 37° C. until the OD600 was 0.4–0.6. Samples were removed for SDS gel analysis and cultures were induced with 1 ml 100 mM IPTG. Cultures were incubated for three additional hours at 37° C. Cultures were then harvested by centrifugation, supernatants discarded and the cell pellet stored at −70° C. until fusion protein purification.

Purification of pET15b-rCART1 and pET23b-rCART2 fusion proteins

Frozen pET15b-rCART1 and pET23b-rCART2 bacterial pellets, prepared as described above, were resuspended in 40 ml Binding Buffer (5 mM imidazole, 0.5 M NaCl, 20 mM Tris pH 7.5, 5 mM Beta- ME) and sonicated in 5×30 sec bursts with chilling on ice between bursts. Lysates were centrifuged at 10,000 rpm for 20 min at 4° C. and the supernatants discarded. The pellets were resuspended in 20 ml Binding Buffer, resonicated and pelleted as described above. The pellets were resuspended in 10 ml Binding Buffer +6 M Urea and chilled on ice for 60 min. Lysates were centrifuged at 10,000 rpm for 20 min at 4° C., with the supernatants removed and filtered through a 0.45 µm filter to remove non-resuspended particulate matter.

Affinity chromatography was then employed to purify the CART fusion proteins. The two fusion proteins contained the amino acid sequence -HHHHHH- (SEQ ID NO.:17) at either the amino- (pET15b-rCART1) or carboxy- (pET23b-rCART2) terminus. No bacterial proteins are known to contain this sequence. Properties unique to the HHHHHH (SEQ ID NO.:17) sequence allow for binding to the metal, nickel (Ni). Thus, a Ni- NTA agarose column (purchased from Qiagen) allowed for purification of the aforementioned CART fusion proteins to at least 95% purity as are determined by SDS-PAGE analysis.

2 ml of a 50% slurry of Ni-NTA agarose was mixed with 2 ml Milli-Q water and allowed to settle in a column. The water was drained, and the resin rinsed with another 10 ml of Milli-Q water. The resin was then equilibrated with 15 ml Binding Buffer +6 M urea. 10 ml of filtered cell lysate from above was added to the column and mixed on a rotary shaker for 60 min. The agarose resin was allowed to settle and the column drained. The column was then washed sequentially with 3×5 ml Binding Buffer +6 M urea, and 3×7 ml Wash Buffer (20 mM imidazole, 0.5 ml NaCl, 20 mM Tris pH 7.5, 5 mM Beta-ME, 6 M urea). The CART fusion proteins were then eluted in 5 ml Elution Buffer (300 mM imidazole, 0.5 ml NaCl, 20 mM Tris pH 7.5, 5 mM Beta-ME, 6 M urea).

The purification procedure was followed by SDS-PAGE analysis of aliquots of crude bacterial lysates, column load material, column load flow through material, wash material and elution material. The final product was judged to be at least 95% pure.

Stepwise dialysis was then performed to remove the urea from the purified CART fusion proteins, and to allow the material to refold into a proper native configuration. 2 ml of the purified protein was sequentially dialyzed for 45 min in 2×500 ml of 0.5 M NaCl, 20 mM Tris pH 6.5, 0.1% Triton X-100 containing urea at concentrations of 4 M, 2 M, 1 M, 0.5 M and 0 M. Additional dialysis was performed for 60 min in 2×1000 ml 0.5 M NaCl, 20 mM Tris pH 6.5, 0.1% Triton X-100, 0.5% glycerol.

Example 8

Production of Human CART Proteins in Bacteria

The procedure of Example 7 is repeated substituting the coding region of human CART cDNA (SEQ ID No.:7) for the rat CART cDNA. A human CART fusion protein is obtained.

Example 9

Generation of Rabbit Polyclonal Antisera Against Synthetic CART Peptides

The following peptides, where underlined areas represent amino acids contained within the rat CART amino acid sequence of SEQ ID No.:4, and non-underlined residues (C and/or Y) represent residues placed at the N-terminus for purposes of enhanced antibody generation (C) or subsequent radiolabeling with iodine (Y), were synthesized using conventional techniques:

| | |
|---|---|
| CQEDAELQPRALDIY | referred to as C-15-Y(SEQ ID No.: 18) |
| CYRRQLRAPGAVLQ | referred to as C-14-Q(SEQ ID No.: 19) |
| CLKSKRIPIYEKKYG | referred to as C-15-G(SEQ ID No.: 20) |
| YGARIGKLCDCPRGTSC | referred to as Y-17-C(SEQ ID No.: 21) |

Polyclonal antisera to the synthetic peptides was produced using conventional techniques, as follows. Primary (500 µg of synthetic peptide) and secondary (250 µg of synthetic peptide) injections of each synthetic peptide were made into each of two female New Zealand white rabbits on days 1 and 16, respectively, with boost injections (250 µg of synthetic peptide) being made on days 37, 58, 79 and 100, post primary injection. On days 47, 68, 89 and 110, post primary injection, each animal was bled and serum was obtained in a conventional manner.

The resulting antisera were designated as follows: Antibodies R1 and R2 were raised against synthetic peptide C-14-Q; Antibodies R3 and R4 were raised against synthetic peptide C-15-Y; Antibodies R5 and R6 were raised against synthetic peptide C-15-G; and Antibodies R7 and R8 were raised against synthetic peptide Y-17-C.

100 ng of affinity purified pET15b-rCART1 and pET23b-rCART2, prepared as described in Example 7, were separated on a 15% SDS-polyacrylamide gel and blotted onto nitrocellulose (Amersham) using semi-dry electrophoretic transfer (Biorad). The blots were blocked overnight at 4° C. in 5% non-fat dry milk in TBS-T (0.2% Tween/Tris-buffered saline). The blots were then rinsed with TBS-T followed by incubation for 2 hours at room temperature in TBS-T including a 1:1000 dilution of one of the primary antisera (R1–R8) or preimmune sera (serving as a negative control). The blots were then rinsed with TBS-T and incubated for 1 hour in TBS-T containing a 1:2000 dilution of secondary antibody (goat anti- rabbit antibodies supplied as a horseradish peroxidase conjugate - Biorad). The blots were again rinsed with TBS-T, and any antigen- primary antibody-secondary antibody complex detected using the ECL detection system (Amersham). Finally, the blots were exposed to Kodak XAR-5 x-ray film for approximately 30 seconds to detect immunoreactive products.

The presence of an approximately 14 kD immunoreactive band representing pET15b-rCART1, and an approximately 17 kD immunoreactive band representing pET23b-rCART2 indicated the presence of corresponding antibodies in the samples tested. For R6, no such signals were present when preimmune sera was tested, while robust signals of appropriate size were observed when the immune sera was tested. Thus, R6 antisera contained antibodies which detected both rCART1 and rCART2 fusion proteins, and represented an effective antisera. R3 and R7 antisera, on the other hand, showed no difference between preimmune and immune sera, and were concluded to be of no value for specific recognition of rCART proteins.

In addition, it was observed that in some Ab lanes, immunoreactive material was present representing higher molecular weight proteins. It was concluded that this material represents concatemerized material, in that the observed molecular weight of this material is identical to multiples (i.e., 2×, 3×, etc.) of the predicted rCART molecular weight.

Example 10

Production of Vaccinia Virus (VV) Expressing Rat CART rCART1 (SEQ ID No.:6) and rCART2 (SEQ ID No.:4) cDNA, including the entire protein coding region as well as some additional 3' and 5' untranslated region, was subcloned into the plasmid pZVneo to facilitate transfer and recombination into vaccinia virus, using the method of Van Slyke et al., supra, the disclosure of which is incorporated herein by reference. For this subcloning, PCR oligos were designed to engineer a BamHI restriction site onto the 5' end of the amplified cDNA, and an XhoI restriction site onto the 3' end of the amplified cDNA. Using full length rCART cDNAs in pBluescript SK– as templates, the cDNAs were PCR amplified employing Vent DNA polymerase (New England Biolabs), digested with BamHI and XhoI, and ligated into pZVneo. These resulting constructs were subsequently subjected to full nucleotide sequence analysis employing a variety of oligonucleotide primers to ensure that no errors had arisen within the resulting CART cDNAs during PCR amplification. These plasmid constructs were then transferred into vaccinia virus in BSC40 cells for production of high titer VV:rCART1 and VV:rCART2 virus vectors by the method of Van Slyke et al., supra.

Detection of rCART1 and rCART2 By Immunoprecipitation Following VV:rCART1 and VV:rCART2 Infection of Cultured Mammalian Cells 10 cm plates containing ~$10^7$ cells were infected at an MOI (multiplicity of infection) of 5 in PBS supplemented with BSA. BSC40 cells (African green Monkey kidney cell line) were incubated with the VV recombinants described above for 30 min at room temperature. VV-containing media was then replaced with DMEM media supplemented with dialyzed 10% fetal calf serum (FCS), Gentamicin and 500µ Ci of EXPRESS protein labeling mix (i.e., 35S-Met and 35SCys, Dupont-NEN) for metabolic labeling of the VV-infected cells. The infected cells were then incubated overnight at 37° C. Negative controls included mock infected cells (no VV) or cells infected with VV:furin to test for crossreactivity of CART antisera against VV proteins. Culture media was removed and centrifuged for 10 min at 3,000 rpm to clear cellular debris followed by storage at –20° C. The infected cells were rinsed in PBS, lysed on the plate in 1 ml cold lysis buffer (1% Triton X-100, 150 mM NaCl, 50 mM Tris pH 7.6), and the lysate collected into 1 ml Eppendorf tubes. The lysate was then centrifuged for 20 min at 4° C., and the supernatants transferred to fresh tubes and stored at –20° C.

To detect radiolabelled rCART1 and rCART2 immunoprecipitation was performed. 300–500 µl of cell lysates and 900 µl of cell culture media were brought to a total volume of 1 ml with 1×lysis buffer or 10×lysis buffer, respectively, followed by incubation with 100 µl of rCART-specific antisera (or pre immune sera). The mixture was then placed on a rotating platform for 2 hours at 4° C. 30 µl of Sepharose A-agarose beads (Zymed) was then added, followed by incubation for an additional 2 hours. The beads were then pelleted and washed 4 times with 1 ml ice cold 1×lysis buffer. The beads were subsequently resuspended in 30 µl of SDS sample buffer (60 mM Tris pH 6.8, 25% glycerol, 2% SDS, 0.1% bromophenol blue, 0.7 M B-mercaptoethanol) and boiled for 5 min. 15 µl of the sample was then subjected to electrophoresis on a 15% SDS-PAGE gel. Following electrophoresis the gels were fixed, followed by incubation in Amplify (Amersham) autoradiographic enhancement solution. The gels were then dried and subjected to autoradiographic analysis to detect the presence of radiolabeled, immunoprecipitated, 35S radiolabeled rCART1 or rCART2.

For VV:rCART2 infected cells, an immunoprecipitated product approximately 17 kD in size was observed in the cellular sample and media sample, indicative of rCART2. This product was not observed when preimmune sera was used. Likewise, for VV:rCART1 infected cells, an immunoprecipitated product approximately 14 kD in size was observed in the cellular sample and media sample, indicative of rCART1. The product was not observed when preimmune sera was used. Thus, VV:CART infected cells appear to make CART protein of predicted size, and furthermore this material appears to be secreted into the media as predicted by the presence of a signal sequence at the N-terminus of the predicted rCART protein. Additionally, these bands were not observed in both mock infected cells (indicating that the aforementioned bands are not BSC40 proteins), and VV:Furin infected cells (indicating that the aforementioned bands are not derived from the Vaccinia virus genome).

The foregoing procedure was repeated by incubating AtT20 cells with the VV recombinants for 2 hours at 30° C., in place of the BSC40 cells. Similar results were obtained. Thus, these results and conclusions are not specific for BSC40 cells, but suggest that the deduced properties of rCART are common to all mammalian cells expressing CART.

Pulse/Chase labeling of VV infected cells

As a further experiment, VV infections of AtT20 and BSC40 cells were carried out as described above, with cells incubated overnight at 37° C. in complete DMEM supplemented with 10% fetal calf serum. Prior to radiolabeling, VV-infected cells were rinsed with and incubated in cysteine- and methionine-deficient DMEM for 15 min. Cells were then pulse-labeled for 45 min with cys/met free DMEM supplemented with 500 µCi EXPRESS protein labeling mix. Labeling media was replaced with complete DMEM +10% FCS (the chase) and cells were harvested following a 30 min, 90 min, 180 min, and 5 hour incubation period. Media and cell harvests were performed as described above. Radiolabeled proteins from cell extracts (c) or media (m) were immunoprecipitated with R6 antisera. Immunoprecipitated products of approximately 17 kD represented CART2 immunoreactive material, while immunoprecipitated products of approximately 14 kD represented CART1 immunoreactive material. For both cell lines and VV recombinants tested, a time-dependent movement of pulse-labeled CART from inside the infected cells to the culture media was observed. As time progressed, less CART material was present in the cells, and more material was found in the media. Thus, CART proteins were determined to migrate from inside to cell to outside the cell in a time dependent manner, indicating that eukaryotic cells secrete CART protein, and that CART may exert its biological activity via release and subsequent interaction with target cells. This finding confirms that originally predicted by the presence of a hydrophobic signal sequence at the amino-terminus of the predicted CART protein as deduced from the original nucleotide sequence analysis. The additional 13 amino acids in rCART2 protein appear to have no effect on this biochemical property.

Patterns of Secretion of rCART1 and rCART2 Following Cell Stimulation

Two distinct types of secretory pathways are found in eukaryotic cells; regulated and constitutive release. Regulated release usually occurs in cells containing dense-core secretory granules in which molecules are stored and released following some type of major stimulatory event. Constitutive release usually does not involve dense-core secretory granules, and represents the means by which molecules are slowly released from cells in a more uniform fashion. To determine how CART might be released from cells, use was made of the fact that AtT20 cells have both constitutive and regulated secretory pathways, but BSC40 cells contain only the constitutive secretory pathway. In the regulatory secretory pathway, depolarization of the cell (such as by the addition of high extracellular potassium, K) causes stored material to be released in a huge bolus. Alternately, in the constitutive pathway, depolarization has no such effect. Thus, the effect of extracellular potassium on AtT20 and BSC40 cells infected with VV:CART virus, the fate of CART proteins, and the type of secretory pathway through which CART is released was determined as follows.

AtT20 or BSC40 cells were infected with VV:rCART1 or VV:rCART2, as described above. Following infection, the cells were pulsed with radiolabeled amino acids for 45 min, followed by a 45 min chase. The chase media (labeled as 'chase') was then collected for analysis, and a second chase media added either containing (+) or not containing (−) KCl for an additional 10 min. After this incubation period, the cells and second chase media were collected for analysis.

Immunoprecipitated products of approximately 17 kD represented CART2 immunoreactive material, while immunoprecipitated products of approximately 14 kD represented CART1 immunoreactive material. For both cell lines and VV recombinants tested, KCl appeared to have no effect on the levels of CART proteins present in either the cells or the second chase media. If CART were present in secretory granules with release occurring through the regulated secretory pathway, then KCl addition would have been expected to increase levels of CART in the stimulated media while decreasing levels of cellular CART. This was not observed. Rather, KCl addition had no apparent effect on media and cellular levels of CART produced in both AtT20 cells and BSC40 cells. Thus, CART not only appears to be secreted from mammalian cells, but secreted by means of constitutive release. Also, the additional 13 amino acids in rCART2 protein appear to have no effect on this biochemical property of the CART protein.

Example 11

Production of Vaccinia Virus Expressing Human CART

The procedure of Example 10 is repeated substituting human CART cDNA (SEQ ID No.:7) for the rat CART cDNA of Example 10. Human CART protein is expressed by the infected cells, and similar results are obtained.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A purified and isolated CART nucleic acid comprising a nucleotide sequence selected from the group consisting of:
   a) a nucleotide sequence as shown in FIG. 1 (SEQ ID No.:3), FIG. 2 (SEQ ID No.:7), or FIG. 3 (SEQ ID No.:9);
   b) a nucleotide sequence which hybridizes under stringent conditions to a nucleotide sequence defined in (a) wherein stringent hybridization conditions comprise incubation at 42° C. in hybridization buffer comprising 400 mM sodium phosphate (pH 7.0), and 50% formamide; and c) a nucleotide sequence encoding the same polypeptide as encoded by the nucleotide sequences of (a) or (b) by means of degenerate codons.

2. A nucleotide sequence of claim 1 which comprises a cDNA sequence that encodes the human CART polypeptide of SEQ ID No.:8 or the rat CART polypeptide of SEQ ID No.:4 or SEQ ID No.:6.

3. A nucleotide sequence of claim 2 which is selected from the group consisting of the sequence of SEQ ID No.:7 and SEQ ID No.:3.

4. A nucleotide sequence of claim 1 which comprises a genomic sequence that encodes the human CART polypeptide of SEQ ID No.:8 or the rat CART polypeptide of SEQ ID No.:4.

5. A nucleotide sequence of claim 4 which comprises the sequence of SEQ ID No.:9.

6. A procaryotic or eucaryotic host cell transformed or transfected with a nucleotide sequence according to claim 1.

7. A viral or circular plasmid comprising a DNA sequence according to claim 1.

8. A viral or circular DNA plasmid according to claim 7 further comprising an expression control DNA sequence operatively associated with said CART encoding DNA.

9. A host cell comprising a plasmid of claim 7.

10. A host cell comprising a plasmid of claim 8.

* * * * *

UNITED STATES PATENT AND TRADEMARK OFFICE
CERTIFICATE OF CORRECTION

Page 1 of 4

PATENT NO. : 5,798,258
DATED : August 25, 1998
INVENTOR(S) : J.O. Douglass

It is certified that error appears in the above-indentified patent and that said Letters Patent is hereby corrected as shown below:

On the title page item

| | | |
|---|---|---|
| [56]<br>Pg. 1, col. 1 | Refs. Cited<br>(Publs., item 1) | "Addition:" should read --Addiction:-- |
| [56]<br>Pg. 1, col. 2 | Refs. Cited<br>(Publs., item 16) | "(1995." should read --(1995).-- |
| [56]<br>Pg. 1, col. 2 | Refs. Cited<br>(Publs., item 19) | "Ny" should read --NY-- |

In the drawings,

| | | |
|---|---|---|
| Fig. 3B | Sheet 6 of 8,<br>last line | After "114", "J C K" should read --K C L-- |

| Column | Line | |
|---|---|---|
| 1 | 40 | "et al," should read --et al.,-- |
| 1 | 47 | After "J" insert --.-- |
| 1 | 64 | After "J" insert --.-- |
| 2 | 24 | "Protein-i 1" should read --Protein-1-- |
| 4 | 9 | After "2A-2B" insert --,-- |
| 4 | 38 | "FIGS. 1 and 2," should read --FIGS. 1A-1B and 2A-2B,-- |
| 4 | 63 | "FIG." should read --FIGS.-- |

UNITED STATES PATENT AND TRADEMARK OFFICE
CERTIFICATE OF CORRECTION

PATENT NO. : 5,798,258
DATED : August 25, 1998
INVENTOR(S) : J.O. Douglass

It is certified that error appears in the above-indentified patent and that said Letters Patent is hereby corrected as shown below:

| COLUMN | LINE | |
|---|---|---|
| 5 | 5 | "FIG." should read --FIGS.-- |
| 5 | 17 | "FIG." should read --FIGS.-- |
| 5 | 28 | "FIG." should read --FIGS.-- |
| 6 | 52 | "an CART" should read --a CART-- |
| 7 | 1 | "5'$T_{11}$CA" should read --5'-$T_{11}$CA-- |
| 8 | 43 | "FIG." should read --FIGS.-- |
| 8 | 43 | After "2A-2B" insert --,-- |
| 10 | 14 | "FIG." should read --FIGS.-- |
| 10 | 14 | After "1A-1B" insert --,-- |
| 10 | 26 | "J" should read --$J$.-- |
| 10 | 38 | After "$J$" insert --.-- |
| 10 | 46 | After "$J$" insert --.-- |
| 10 | 66 | After "$J$" insert --.-- |

UNITED STATES PATENT AND TRADEMARK OFFICE
CERTIFICATE OF CORRECTION

PATENT NO. : 5,798,258
DATED : August 25, 1998
INVENTOR(S) : J.O. Douglass

It is certified that error appears in the above-indentified patent and that said Letters Patent is hereby corrected as shown below:

| COLUMN | LINE | |
|---|---|---|
| 11 | 17 | "FIG." should read --FIGS.-- |
| 11 | 51 | "(V691)" should read --(V69I)-- |
| 14 | 49 | "mg/mil" should read --mg/ml-- |
| 15 | 40 | "FIG." should read --FIGS.-- |
| 16 | 33 | "*J Histotechnol,*" should read --*J. Histotechnol.,*-- |
| 16 | 65 | "PstI/HincII)" should read --PstI/HincII)-- |
| 20 | 26 | "mg/mi" should read --mg/ml-- |
| 21 | 45 | "pET15-rCART1" should read --*pET15b-rCART1*-- |
| 22 | 10 | "QED . . . (rCART1) . . . KCl" should read --*QED . . . (rCART1) . . . KCL*-- |
| 22 | 13 | "QED . . . (rCART1) . . . KCL" should be in character italics |
| 22 | 63 | "QED . . . (rCART2) . . . KCL" should be in character italics |

UNITED STATES PATENT AND TRADEMARK OFFICE
CERTIFICATE OF CORRECTION

PATENT NO. : 5,798,258
DATED : August 25, 1998
INVENTOR(S) : J.O. Douglass

It is certified that error appears in the above-indentified patent and that said Letters Patent is hereby corrected as shown below:

| COLUMN | LINE | |
|--------|------|---|
| 22 | 66 | "QED . . . (rCART2) . . . KCL" should be in character italics |
| 25 | 30-31 | Insert a line space between "supra." and "Detection" |
| 26 | 58 | "inside to cell" should read --inside the cell-- |

Signed and Sealed this

Fifteenth Day of June, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( x i ) SEQUENCE DESCRIPTION: SEQ ID NO:1:

ACGTCTCATG        10

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( x i ) SEQUENCE DESCRIPTION: SEQ ID NO:2:

GCTTTTTTTT TTT                                                                                                13

(2) INFORMATION FOR SEQ ID NO:3:

(i) SEQUENCE CHARACTERISTICS:
       (A) LENGTH: 840 base pairs
       (B) TYPE: nucleic acid
       (C) STRANDEDNESS: single
       (D) TOPOLOGY: linear (ii) MOLECULE TYPE: cDNA to mRNA (iii) HYPOTHETICAL: NO (ix) FEATURE:
       (A) NAME/KEY: polyA_site
       (B) LOCATION: 548..553
       (D) OTHER INFORMATION: /note= "Poly(A) site for approximately
           700 base rat CART transcript"

(ix) FEATURE:
       (A) NAME/KEY: polyA_site
       (B) LOCATION: 814..819
       (D) OTHER INFORMATION: /note= "Alternate Poly(A) site for
           approximately 900 base rat CART transcr..."

(ix) FEATURE:
       (A) NAME/KEY: CDS
       (B) LOCATION: 20..409

(ix) FEATURE:
       (A) NAME/KEY: primer_bind
       (B) LOCATION: 158..167
       (D) OTHER INFORMATION: /note= "5' PCR differential display
           primer hybridization site"

(ix) FEATURE:
       (A) NAME/KEY: primer_bind
       (B) LOCATION: 544..556
       (D) OTHER INFORMATION: /note= "3' PCR differential display
           primer hybridization site"

(ix) FEATURE:
       (A) NAME/KEY: misc_feature
       (B) LOCATION: 179..217
       (D) OTHER INFORMATION: /note= "Alternatively spliced 39
           nucleotide sequence"

(xi) SEQUENCE DESCRIPTION: SEQ ID NO:3:

```
AGCGAGGAAG TCCAGCACC ATG GAG AGC TCC CGC CTG CGG CTG CTA CCC GTC           52
                    Met Glu Ser Ser Arg Leu Arg Leu Leu Pro Val
                     1               5                  10

CTG GGC GCC GCC CTA CTG CTG CTG CTA CCT TTG CTG GGT GCC GGT GCC           100
Leu Gly Ala Ala Leu Leu Leu Leu Leu Pro Leu Leu Gly Ala Gly Ala
             15                  20                  25

CAG GAG GAT GCC GAG CTG CAG CCC CGA GCC CTG GAC ATC TAC TCT GCC           148
Gln Glu Asp Ala Glu Leu Gln Pro Arg Ala Leu Asp Ile Tyr Ser Ala
         30                  35                  40

GTG GAT GAT GCG TCC CAT GAG AAG GAG CTG CCA AGG CGG CAA CTT CGG           196
Val Asp Asp Ala Ser His Glu Lys Glu Leu Pro Arg Arg Gln Leu Arg
     45                  50                  55

GCT CCC GGC GCT GTG TTG CAG ATT GAA GCG CTG CAG GAA GTC CTG AAG           244
Ala Pro Gly Ala Val Leu Gln Ile Glu Ala Leu Gln Glu Val Leu Lys
 60                  65                  70                  75

AAG CTC AAG AGT AAA CGC ATT CCG ATC TAT GAG AAG AAG TAC GGC CAA           292
Lys Leu Lys Ser Lys Arg Ile Pro Ile Tyr Glu Lys Lys Tyr Gly Gln
                 80                  85                  90

GTC CCC ATG TGT GAC GCT GGA GAG CAG TGC GCA GTG CGG AAA GGG GCC           340
Val Pro Met Cys Asp Ala Gly Glu Gln Cys Ala Val Arg Lys Gly Ala
             95                 100                 105

AGG ATC GGG AAG CTG TGT GAC TGT CCC CGA GGA ACT TCT TGC AAT TCT           388
```

|     |     |     |     |     |     |     |     |     |     |     |     |     |     |     |
|---|---|---|---|---|---|---|---|---|---|---|---|---|---|---|
| Arg | Ile | Gly | Lys | Leu | Cys | Asp | Cys | Pro | Arg | Gly | Thr | Ser | Cys | Asn | Ser |
|     |     | 110 |     |     |     | 115 |     |     |     |     | 120 |     |     |     |

```
TTC CTC TTG AAG TGC TTG TGAAGGGGTG ACAGCCTCCT TCGGTTCCCA            436
Phe Leu Leu Lys Cys Leu
    125                 130

TATTTCCTCT TTCCCCTAAA GGAGCGCTCT TTTGTCCTG GAGCCGCTTT AACAACAATA     496

AAGTTTGCGT TCCCCCAGA GAGTGGATGG GCTCTTTCCC TGCTGCTTCA AAATAAAAGA     556

TTTGATGTTA TTGTGTGAAG GACAATACCT TGAATGGTGT TGGTATGTGT GCAAAGTATT    616

CTTCTCTCGT TTATCCACC TGACACATTC TTGTGACCTT TCTGGAAGA AGAGGGACTT      676

TCGCTTTAAA ACTGTATTTT TGTATGTGGC GGGTCACAAT GAAGATTAGA CCTAGTTAAT    736

TTTGGCAGAT GACATCATAA CCCGGAAAAC AAATCACCCC AAAGCAACAC AAATGGAAGC    796

ATGTGCAAAT TACACCCAAT AAAGCATTTT TGATAATTGC TCAC                    840
```

(2) INFORMATION FOR SEQ ID NO:4:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Ser Ser Arg Leu Arg Leu Leu Pro Val Leu Gly Ala Ala Leu
 1               5                  10                  15

Leu Leu Leu Leu Pro Leu Leu Gly Ala Gly Ala Gln Glu Asp Ala Glu
             20                  25                  30

Leu Gln Pro Arg Ala Leu Asp Ile Tyr Ser Ala Val Asp Asp Ala Ser
         35                  40                  45

His Glu Lys Glu Leu Pro Arg Arg Gln Leu Arg Ala Pro Gly Ala Val
     50                  55                  60

Leu Gln Ile Glu Ala Leu Gln Glu Val Leu Lys Lys Leu Lys Ser Lys
 65                  70                  75                  80

Arg Ile Pro Ile Tyr Glu Lys Lys Tyr Gly Gln Val Pro Met Cys Asp
                 85                  90                  95

Ala Gly Glu Gln Cys Ala Val Arg Lys Gly Ala Arg Ile Gly Lys Leu
            100                 105                 110

Cys Asp Cys Pro Arg Gly Thr Ser Cys Asn Ser Phe Leu Leu Lys Cys
            115                 120                 125

Leu
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Pro Arg Arg Gln Leu Arg Ala Pro Gly Ala Val Leu Gln
 1               5                  10
```

(2) INFORMATION FOR SEQ ID NO:6:

(i) SEQUENCE CHARACTERISTICS:
        (A) LENGTH: 116 amino acids (B) TYPE: amino acid
(C) STRANDEDNESS: single
(D) TOPOLOGY: linear (i i) MOLECULE TYPE: protein (x i) SEQUENCE DESCRIPTION: SEQ ID NO:6:

```
Met Glu Ser Ser Arg Leu Arg Leu Leu Pro Val Leu Gly Ala Ala Leu
 1               5                  10                  15

Leu Leu Leu Leu Pro Leu Leu Gly Ala Gly Ala Gln Glu Asp Ala Glu
             20                  25                  30

Leu Gln Pro Arg Ala Leu Asp Ile Tyr Ser Ala Val Asp Asp Ala Ser
         35                  40                  45

His Glu Lys Glu Leu Ile Glu Ala Leu Gln Glu Val Leu Lys Lys Leu
     50                  55                  60

Lys Ser Lys Arg Ile Pro Ile Tyr Glu Lys Lys Tyr Gly Gln Val Pro
 65                  70                  75                  80

Met Cys Asp Ala Gly Glu Gln Cys Ala Val Arg Lys Gly Ala Arg Ile
                 85                  90                  95

Gly Lys Leu Cys Asp Cys Pro Arg Gly Thr Ser Cys Asn Ser Phe Leu
            100                 105                 110

Leu Lys Cys Leu
        115
```

(2) INFORMATION FOR SEQ ID NO:7:

(i) SEQUENCE CHARACTERISTICS:
(A) LENGTH: 800 base pairs
(B) TYPE: nucleic acid
(C) STRANDEDNESS: single
(D) TOPOLOGY: linear (i i) MOLECULE TYPE: cDNA
(A) DESCRIPTION: human CART cDNA (FIGURE 2)

(i i i) HYPOTHETICAL: NO (i x) FEATURE:
(A) NAME/KEY: CDS
(B) LOCATION: 20..370

(x i) SEQUENCE DESCRIPTION: SEQ ID NO:7:

```
AACGACGAGT TCAGAACG ATG GAG AGC TCC CGC GTG AGG CTG CTG CCC CTC      52
                    Met Glu Ser Ser Arg Val Arg Leu Leu Pro Leu
                     1               5                  10

CTG GGC GCC GCC CTG CTG CTG ATG CTA CCT CTG TTG GGT ACC CGT GCC     100
Leu Gly Ala Ala Leu Leu Leu Met Leu Pro Leu Leu Gly Thr Arg Ala
             15                  20                  25

CAG GAG GAC GCC GAG CTC CAG CCC CGA GCC CTG GAC ATC TAC TCT GCC     148
Gln Glu Asp Ala Glu Leu Gln Pro Arg Ala Leu Asp Ile Tyr Ser Ala
         30                  35                  40

GTG GAT GAT GCC TCC CAC GAG AAG GAG CTG ATC GAA GCG CTG CAA GAA     196
Val Asp Asp Ala Ser His Glu Lys Glu Leu Ile Glu Ala Leu Gln Glu
 45                  50                  55

GTC TTG AAG AAG CTC AAG AGT AAA CGT GTT CCC ATC TAT GAG AAG AAG     244
Val Leu Lys Lys Leu Lys Ser Lys Arg Val Pro Ile Tyr Glu Lys Lys
 60                  65                  70                  75

TAT GGC CAA GTC CCC ATG TGT GAC GCC GGT GAG CAG TGT GCA GTG AGG     292
Tyr Gly Gln Val Pro Met Cys Asp Ala Gly Glu Gln Cys Ala Val Arg
                 80                  85                  90

AAA GGG GCA AGG ATC GGG AAG CTG TGT GAC TGT CCC CGA GGA ACC TCC     340
Lys Gly Ala Arg Ile Gly Lys Leu Cys Asp Cys Pro Arg Gly Thr Ser
             95                 100                 105
```

-continued

```
TGC AAT TCC TTC CTC CTG AAG TGC TTA TGAAGGGGCG TCCATTCTCC          387
Cys Asn Ser Phe Leu Leu Lys Cys Leu
    110                 115

TCCATACATC CCCATCCCTC TACTTTCCCC AGAGGACCAC ACCTTCCTCC CTGGAGTTTG   447

GCTTAAGCAA CAGATAAAGT TTTTATTTTC CTCTGAAGGG AAAGGGCTCT TTTCCTGCTG   507

TTTCAAAAAT AAAAGAACAC ATTAGATGTT ACTGTGTGAA GAATAATGCC TTGTATGGTG   567

TTGATACGTG TGTGAAGTAT TCTTATTTTA TTTGTCTGAC AAACTCTTGT GTACCTTTGT   627

GTAAAGAAGG GAAGCTTTGT TTGAAAATTG TATTTTTGTA TGTGGCATGG CAGAATGAAA   687

ATTAGATCTA GCTAATCTCG GTAGATGTCA TTACAACCTG GAAAATAAAT CACCCTAAGT   747

GACACAAATT GAAGCATGTA CAAATTATAC ATAATAAAGT GTTTTAATA ATT        800
```

(2) INFORMATION FOR SEQ ID NO:8:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:8:

```
Met Glu Ser Ser Arg Val Arg Leu Leu Pro Leu Leu Gly Ala Ala Leu
 1           5                  10                  15

Leu Leu Met Leu Pro Leu Leu Gly Thr Arg Ala Gln Glu Asp Ala Glu
            20                  25                  30

Leu Gln Pro Arg Ala Leu Asp Ile Tyr Ser Ala Val Asp Asp Ala Ser
        35                  40                  45

His Glu Lys Glu Leu Ile Glu Ala Leu Gln Glu Val Leu Lys Lys Leu
    50                  55                  60

Lys Ser Lys Arg Val Pro Ile Tyr Glu Lys Lys Tyr Gly Gln Val Pro
65                  70                  75                  80

Met Cys Asp Ala Gly Glu Gln Cys Ala Val Arg Lys Gly Ala Arg Ile
                85                  90                  95

Gly Lys Leu Cys Asp Cys Pro Arg Gly Thr Ser Cys Asn Ser Phe Leu
                100                 105                 110

Leu Lys Cys Leu
            115
```

(2) INFORMATION FOR SEQ ID NO:9:

(i) SEQUENCE CHARACTERISTICS:
        (A) LENGTH: 2483 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: human CART genome DNA (iii) HYPOTHETICAL: NO (ix) FEATURE:
        (A) NAME/KEY: promoter
        (B) LOCATION: 72..77

(ix) FEATURE:
        (A) NAME/KEY: CDS
        (B) LOCATION: join(122..280, 706..789, 1329..1436)

(ix) FEATURE:
        (A) NAME/KEY: intron
        (B) LOCATION: 281..705

( i x ) FEATURE:
    ( A ) NAME/KEY: intron
    ( B ) LOCATION: 790..1328

( i x ) FEATURE:
    ( A ) NAME/KEY: polyA_site
    ( B ) LOCATION: 1581..1586

( i x ) FEATURE:
    ( A ) NAME/KEY: polyA_site
    ( B ) LOCATION: 1797..1802

( i x ) FEATURE:
    ( A ) NAME/KEY: polyA_site
    ( B ) LOCATION: 1846..1851

( x i ) SEQUENCE DESCRIPTION: SEQ ID NO:9:

```
CCCGGGCCCT CCTCCACCCC CCCTTCCTTC TTCGCCTCCT CCCTCTTTCC TGCACGGGGG          60

CTCGGGCTCA CTATAAAGG TGGGAGCGCG TGGTGCCCCA GCAACGACGA GTTTCAGAAC          120

G ATG GAG AGC TCC CGC GTG AGG CTG CTG CCC CTC CTG GGC GCC GCC             166
  Met Glu Ser Ser Arg Val Arg Leu Leu Pro Leu Leu Gly Ala Ala
  1               5                   10                  15

CTG CTG CTG ATG CTA CCT CTG TTG GGT ACC CGT GCC CAG GAG GAC GCC           214
Leu Leu Leu Met Leu Pro Leu Leu Gly Thr Arg Ala Gln Glu Asp Ala
                20                  25                  30

GAG CTC CAG CCC CGA GCC CTG GAC ATC TAC TCT GCC GTG GAT GAT GCC           262
Glu Leu Gln Pro Arg Ala Leu Asp Ile Tyr Ser Ala Val Asp Asp Ala
            35                  40                  45

TCC CAC GAG AAG GAG CTG GTCGGTATTC CCCTCGCTCT CGACCCCCTT                  310
Ser His Glu Lys Glu Leu
                50

GACGTGTCGC CTTGTCTCTT CTCTTGCACG CCTCCCTCCT TCCCCCCACC CCCACTCCTA         370

TTCCCAGAGT CAGGGCGCGG GGAGCTGAGC GCAACGCCCA GGCACCCACT GCCATCCGAA         430

GAGCGACTCG AGCTCACGGG CTCCTGGCAG TCTGTTGAGC GAATCCCTCA TCCCGGCCCC         490

TCTGAGCAAC AGGGGCCCCA GCGGCTCAGA GACCCGCGGT CAGTACCTGG ACAGCGTCG          550

CTAAGTTTCC ACCCCTCGAC CATTCCCTGT GTCCGCGGAG TCCCACCGCA GAGTGCGTGT         610

GGGTCCGGGG CTCCTTATAA CTAGGGCTGG AAGTGCGCAC CTGGGCTGGG CTCGCAGCAA         670

GGCGCAACTT CAGGCTCCGA AGCGGTGTGT TGCAG ATC GAA GCG CTG CAA GAA            723
                                        Ile Glu Ala Leu Gln Glu
                                                            55

GTC TTG AAG AAG CTC AAG AGT AAA CGT GTT CCC ATC TAT GAG AAG AAG           771
Val Leu Lys Lys Leu Lys Ser Lys Arg Val Pro Ile Tyr Glu Lys Lys
60                  65                  70                  75

TAT GGC CAA GTC CCC ATG GTAAGGTTTG TGGTCACTCC CTTCCCGTGT                  819
Tyr Gly Gln Val Pro Met
                80

TTTTCCAAGA GAAAGTACAC CGCCTTGAAT CGTACACACA GCTCCGTAGG ATGTGGCTAA         879

ATAACTTAGG TAATGGGCTT GCAGGATTCT GTGGGCTCCT TCTTCCTTCC CGGGTGAGGA         939

AATGGGAAAG CAGGAACAGG GGTTGTAAGA AAGTGTAAGT CTATTGTTTG TTGCTCAGGA         999

AAAAGGTCTG ATTTTTTTCC CTCTGAGAGG GCAAGAAAAG GAGCCAGGAA ATGTGATGCT         1059

CCCCTTCCCA CGCCCCCCAA CCCTCGCCAC TTAAAGGTGG AAGAAACTAG GATAAAACTA        1119

ATAATGTAAG TTTCTTTAAA AAATGTACTC TCACTGAGGT TATAAGCACA AGGCTCCCTG        1179

TTTCAGATCT GACTGTACGT CGACCTCTTG TGATGGTGAT GGGGTCCAAT TGCCCCTTTC        1239

AAGAGACAGA AATTGCGTTG ACTGTGAGAC TTGCCTGTTG GGAACCTGGG TTTGTTCATA        1299

CTCGATGACC ACACATTTTG TTGTTTCAG TGT GAC GCC GGT GAG CAG TGT GCA         1352
                                Cys Asp Ala Gly Glu Gln Cys Ala
```

| | | | | | | | | | | | | | | |
|---|---|---|---|---|---|---|---|---|---|---|---|---|---|---|
| | | | | | | | 85 | | | | | | | |
| GTG | AGG | AAA | GGG | GCA | AGG | ATC | GGG | AAG | CTG | TGT | GAC | TGT | CCC | CGA | GGA | 1400 |
| Val | Arg | Lys | Gly | Ala | Arg | Ile | Gly | Lys | Leu | Cys | Asp | Cys | Pro | Arg | Gly |
| 90 | | | | | 95 | | | | 100 | | | | | 105 |
| ACC | TCC | TGC | AAT | TCC | TTC | CTC | CTG | AAG | TGC | TTA | TGAAGGGGCG | TCCATTCTCC | 1453 |
| Thr | Ser | Cys | Asn | Ser | Phe | Leu | Leu | Lys | Cys | Leu |
| | | | | 110 | | | | | 115 |

```
TCCATACATC  CCCATCCCTC  TACTTTCCCC  AGAGGACCAC  ACCTTCCTCC  CTGGAGTTTG    1513
GCTTAAGCAA  CAGATAAAGT  TTTTATTTTC  CTCTGAAGGG  AAAGGGCTCT  TTTCCTGCTG    1573
TTTCAAAAAT  AAAAGAACAC  ATTAGATGTT  ACTGTGTGAA  GAATAATGCC  TTGTATGGTG    1633
TTGATACGTG  TGTGAAGTAT  TCTTATTTTA  TTTGTCTGAC  AAACTCTTGT  GTACCTTTGT    1693
GTAAAGAAGG  GAAGCTTTGT  TTGAAAATTG  TATTTTTGTA  TGTGGCATGG  CAGAATGAAA    1753
ATTAGATCTA  GCTAATCTCG  GTAGATGTCA  TTACAACCTG  GAAAATAAAT  CACCCTAAGT    1813
GACACAAATT  GAAGCATGTA  CAAATTATAC  ATAATAAAGT  GTTTTAATA   ATTGCCCATA    1873
GTGCACTGCT  GTTTTCATAT  AAGTAATTTA  AGTGGAAATG  GTGAGATTAA  TCATGCTGTT    1933
GTTTTCAAAG  AAAAATATTT  CAAAAATAGC  AGCCTATTGG  AAATGCACTA  CGTCAGAGTT    1993
GATCGTATAG  AGTTGCAGCA  GTTAGTATAC  CTATTCTTG   ATGCAGCGAG  TGTGTGTGTA    2053
TGTGTGTGTG  TTAGTGTGTG  TGTGTGTGTG  TGTGTGAGAG  AGAGAGAGAG  AGAGAAAGAG    2113
AGAGATGAAT  GAGATGGAGA  TGGTTGGAGA  AGAGGTTATA  TAATTTTGTT  TATTAAAACC    2173
TTTAGCCAGA  CCCTTTACTT  TAAACAGTGA  GACCAATAAA  CTATAAACAG  TTTCATGTTT    2233
TAGTCACATT  AAAAGCAATT  TGAAAAATTA  GAAATTTTGT  TTTGACAACT  CCCTTATTAG    2293
AAAATATACA  TTGATTTAAA  GATATGGGCT  GTTTAGGGTT  GTTATTTGTC  TAAAGACTCC    2353
AAGGTTATAA  GACCCATCCA  TCCCACAAGT  AAATTCACAC  TCTTGGAAAA  ATTCTCTATT    2413
CCAGGAGAAA  GAGTCATTTC  AGAAAATAGT  TTTGAGGGGA  ACAAATAAAA  ATTGGAGGAG    2473
GTGAGAATTC                                                                 2483
```

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: N-terminal rCART1 cDNA primer
        ( Example 7 )

( i i i ) HYPOTHETICAL: NO ( x i ) SEQUENCE DESCRIPTION: SEQ ID NO:10:

```
CGATCGGCAT  ATGCAGGAGG  ATGCCGAGCT  G                                        31
```

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: C-terminal rCART1 cDNA primer
        ( Example 7 )

( i i i ) HYPOTHETICAL: NO ( x i ) SEQUENCE DESCRIPTION: SEQ ID NO:11:

CGGCGGATCC GTTAAAGCGG CTCCAGGG 28

( 2 ) INFORMATION FOR SEQ ID NO:12:

( i ) SEQUENCE CHARACTERISTICS:
 ( A ) LENGTH: 30 base pairs
 ( B ) TYPE: nucleic acid
 ( C ) STRANDEDNESS: single
 ( D ) TOPOLOGY: linear ( i i ) MOLECULE TYPE: Other nucleic acid
 ( A ) DESCRIPTION: N-terminal rCART2 cDNA primer
 ( Example 7 )

( i i i ) HYPOTHETICAL: NO ( x i ) SEQUENCE DESCRIPTION: SEQ ID NO:12:

GGTCGGGATC CGCAGGAGGA TGCCGAGCTG 30

( 2 ) INFORMATION FOR SEQ ID NO:13:

( i ) SEQUENCE CHARACTERISTICS:
 ( A ) LENGTH: 30 base pairs
 ( B ) TYPE: nucleic acid
 ( C ) STRANDEDNESS: single
 ( D ) TOPOLOGY: linear ( i i ) MOLECULE TYPE: Other nucleic acid
 ( A ) DESCRIPTION: C-terminal rCART2 cDNA primer
 ( Example 7 )

( i i i ) HYPOTHETICAL: NO ( x i ) SEQUENCE DESCRIPTION: SEQ ID NO:13:

GGTGCTCGAG CAAGCACTTC AAGAGGAAAG 30

( 2 ) INFORMATION FOR SEQ ID NO:14:

( i ) SEQUENCE CHARACTERISTICS:
 ( A ) LENGTH: 13
 ( B ) TYPE: nucleic acid
 ( C ) STRANDEDNESS: single
 ( D ) TOPOLOGY: linear ( i i ) MOLECULE TYPE: Other nucleic acid
 ( A ) DESCRIPTION: Kozak translation initiation sequence element ( i i i ) HYPOTHETICAL: NO ( x i ) SEQUENCE DESCRIPTION: SEQ ID NO:14:[:]

GCCGCCRCCA TGG 13

( 2 ) INFORMATION FOR SEQ ID NO:15:

( i ) SEQUENCE CHARACTERISTICS:
 ( A ) LENGTH: 110 amino acids
 ( B ) TYPE: amino acid
 ( C ) STRANDEDNESS: single
 ( D ) TOPOLOGY: linear ( i i ) MOLECULE TYPE: protein
 ( A ) DESCRIPTION: pET15b-rCART1 fusion protein ( i i i ) HYPOTHETICAL: YES ( x i ) SEQUENCE DESCRIPTION: SEQ ID NO:15:

Met Gly Ser Ser His His His His His His Ser Ser Gly Leu Val Pro
 1               5                  10                  15

Arg Gly Ser His Met Gln Glu Asp Ala Glu Leu Gln Pro Arg Ala Leu

|  | 20 |  |  |  | 25 |  |  |  |  | 30 |  |  |
|---|---|---|---|---|---|---|---|---|---|---|---|---|
| Asp | Ile | Tyr | Ser | Ala | Val | Asp | Asp | Ala | Ser | His | Glu | Lys | Glu | Leu | Ile |
|  | 35 |  |  |  |  | 40 |  |  |  | 45 |  |  |
| Glu | Ala | Leu | Gln | Glu | Val | Leu | Lys | Lys | Leu | Lys | Ser | Lys | Arg | Ile | Pro |
| 50 |  |  |  |  | 55 |  |  |  |  | 60 |  |  |
| Ile | Tyr | Glu | Lys | Lys | Tyr | Gly | Gln | Val | Pro | Met | Cys | Asp | Ala | Gly | Glu |
| 65 |  |  |  |  | 70 |  |  |  |  | 75 |  |  |  |  | 80 |
| Gln | Cys | Ala | Val | Arg | Lys | Gly | Ala | Arg | Ile | Gly | Lys | Leu | Cys | Asp | Cys |
|  |  |  |  | 85 |  |  |  |  | 90 |  |  |  |  | 95 |
| Pro | Arg | Gly | Thr | Ser | Cys | Asn | Ser | Phe | Leu | Leu | Lys | Cys | Leu |
|  |  |  | 100 |  |  |  |  | 105 |  |  |  |  | 110 |

(2) INFORMATION FOR SEQ ID NO:16:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein
        (A) DESCRIPTION: pET23b-rCART2 fusion protein (iii) HYPOTHETICAL: YES (xi) SEQUENCE DESCRIPTION: SEQ ID NO:16:

| Met | Ala | Ser | Met | Thr | Gly | Gly | Gln | Gln | Met | Gly | Arg | Asp | Pro | Gln | Glu |
|---|---|---|---|---|---|---|---|---|---|---|---|---|---|---|---|
|  |  |  |  | 5 |  |  |  |  | 10 |  |  |  |  | 15 |  |
| Asp | Ala | Glu | Leu | Gln | Pro | Arg | Ala | Leu | Asp | Ile | Tyr | Ser | Ala | Val | Asp |
|  |  |  | 20 |  |  |  |  | 25 |  |  |  |  | 30 |  |  |
| Asp | Ala | Ser | His | Glu | Lys | Glu | Leu | Pro | Arg | Arg | Gln | Leu | Arg | Ala | Pro |
|  |  | 35 |  |  |  |  | 40 |  |  |  |  | 45 |  |  |  |
| Gly | Ala | Val | Leu | Gln | Ile | Glu | Ala | Leu | Gln | Glu | Val | Leu | Lys | Lys | Leu |
| 50 |  |  |  |  | 55 |  |  |  |  | 60 |  |  |  |  |  |
| Lys | Ser | Lys | Arg | Ile | Pro | Ile | Tyr | Glu | Lys | Lys | Tyr | Gly | Gln | Val | Pro |
| 65 |  |  |  |  | 70 |  |  |  |  | 75 |  |  |  |  | 80 |
| Met | Cys | Asp | Ala | Gly | Glu | Gln | Cys | Ala | Val | Arg | Lys | Gly | Ala | Arg | Ile |
|  |  |  |  | 85 |  |  |  |  | 90 |  |  |  |  | 95 |  |
| Gly | Lys | Leu | Cys | Asp | Cys | Pro | Arg | Gly | Thr | Ser | Cys | Asn | Ser | Phe | Leu |
|  |  |  | 100 |  |  |  |  | 105 |  |  |  |  | 110 |  |  |
| Leu | Lys | Cys | Leu | Leu | Gly | His | His | His | His | His | His |
|  |  | 115 |  |  |  |  | 120 |  |  |  |  |

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:17:

| His | His | His | His | His | His |
|---|---|---|---|---|---|
| 1 |  |  |  | 5 |  |

(2) INFORMATION FOR SEQ ID NO:18:

(i) SEQUENCE CHARACTERISTICS:
        (A) LENGTH: 15 amino acids ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:18:

Cys Gln Glu Asp Ala Glu Leu Gln Pro Arg Ala Leu Asp Ile Tyr
1               5                   10                  15

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:19:

Cys Tyr Arg Arg Gln Leu Arg Ala Pro Gly Ala Val Leu Gln
1               5                   10

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:20:

Cys Leu Lys Ser Lys Arg Ile Pro Ile Tyr Glu Lys Lys Tyr Gly
1               5                   10                  15

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:21:

Tyr Gly Ala Arg Ile Gly Lys Leu Cys Asp Cys Pro Arg Gly Thr Ser
1               5                   10                  15
Cys